United States Patent
Khairatkar-Joshi et al.

(10) Patent No.: US 9,855,229 B2
(45) Date of Patent: *Jan. 2, 2018

(54) TREATMENT OF RESPIRATORY DISORDERS USING ROR-GAMMA INHIBITORS

(71) Applicant: Glenmark Pharmaceuticals S.A., La Chaux-de-Fonds (CH)

(72) Inventors: Neelima Khairatkar-Joshi, Thane (IN); Abhay Kulkarni, Navi Mumbai (IN); Daisy Manish Shah, Mumbai (IN); Vikram Mansingh Bhosale, Mumbai (IN); Bhavik Jaysukhlal Lodhiya, Rajkot (IN); Alamelu Mangai Thiraviam, Navi Mumbai (IN); Megha Marathe, Thane (IN); Avinash Annaso Hadambar, Satara (IN)

(73) Assignee: GLENMARK PHARMACEUTICALS S.A., La Chaux-de-Fonds (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/169,325

(22) Filed: May 31, 2016

(65) Prior Publication Data
US 2016/0346234 A1 Dec. 1, 2016

(30) Foreign Application Priority Data

May 29, 2015 (IN) .................. 2091/MUM/2015
Mar. 31, 2016 (IN) .................. 201621011426

(51) Int. Cl.
| | | |
|---|---|---|
| A61K 31/167 | (2006.01) | |
| A61K 31/437 | (2006.01) | |
| A61K 31/4184 | (2006.01) | |
| A61K 31/351 | (2006.01) | |
| A61K 31/44 | (2006.01) | |
| A61K 31/404 | (2006.01) | |
| A61K 9/00 | (2006.01) | |
| G01N 33/50 | (2006.01) | |
| A61K 31/35 | (2006.01) | |

(52) U.S. Cl.
CPC ............ *A61K 31/167* (2013.01); *A61K 9/007* (2013.01); *A61K 31/35* (2013.01); *A61K 31/351* (2013.01); *A61K 31/404* (2013.01); *A61K 31/4184* (2013.01); *A61K 31/437* (2013.01); *A61K 31/44* (2013.01); *G01N 33/5088* (2013.01)

(58) Field of Classification Search
None
See application file for complete search history.

(56) References Cited

FOREIGN PATENT DOCUMENTS

| WO | WO-2012027965 A1 | 3/2012 |
|---|---|---|
| WO | WO-2012028100 A1 | 3/2012 |
| WO | WO-2012064744 A2 | 5/2012 |
| WO | WO-2012100732 A1 | 8/2012 |

(Continued)

*Primary Examiner* — Karl J Puttlitz
(74) *Attorney, Agent, or Firm* — Blank Rome LLP

(57) ABSTRACT

The present patent application relates to treatment of a respiratory disorder using retinoid-related orphan receptor gamma t (ROR-gamma) modulators. Particularly, the present patent application relates to treatment of a respiratory disorder using a RORγ inhibitor, wherein the RORγ inhibitor is administered by an inhalation route to a subject in need thereof.

5 Claims, 4 Drawing Sheets

Effect of treatment of Compound 1 on inflammation in BALf of the animals exposed to cigarette smoke

(56) References Cited

FOREIGN PATENT DOCUMENTS

| | | |
|---|---|---|
| WO | WO-2012100734 A1 | 8/2012 |
| WO | WO-2012139775 A1 | 10/2012 |
| WO | 2013171729 * | 11/2013 |
| WO | WO-2013171729 A2 | 11/2013 |
| WO | 2015/159233 * | 10/2015 |

* cited by examiner

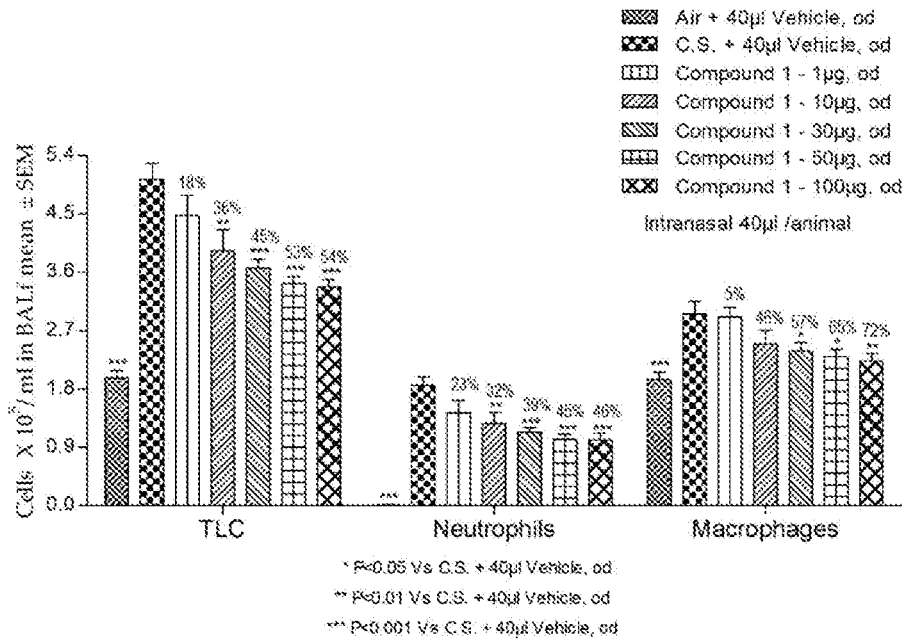
Figure 1: Effect of treatment of Compound 1 on inflammation in BALf of the animals exposed to cigarette smoke
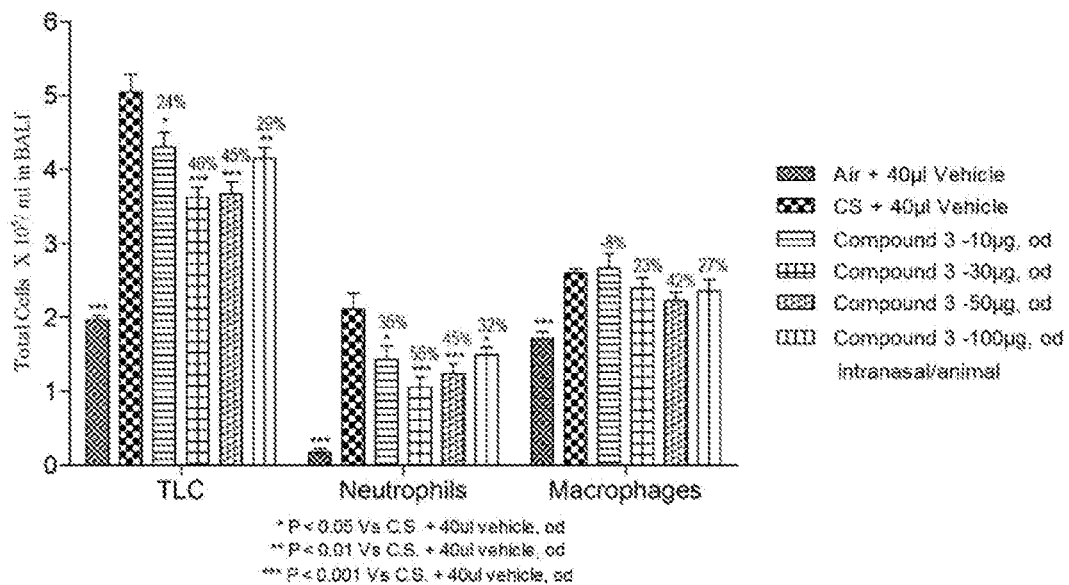
Figure 2: Effect of treatment of Compound 3 on inflammation in BALf of the animals exposed to cigarette smoke

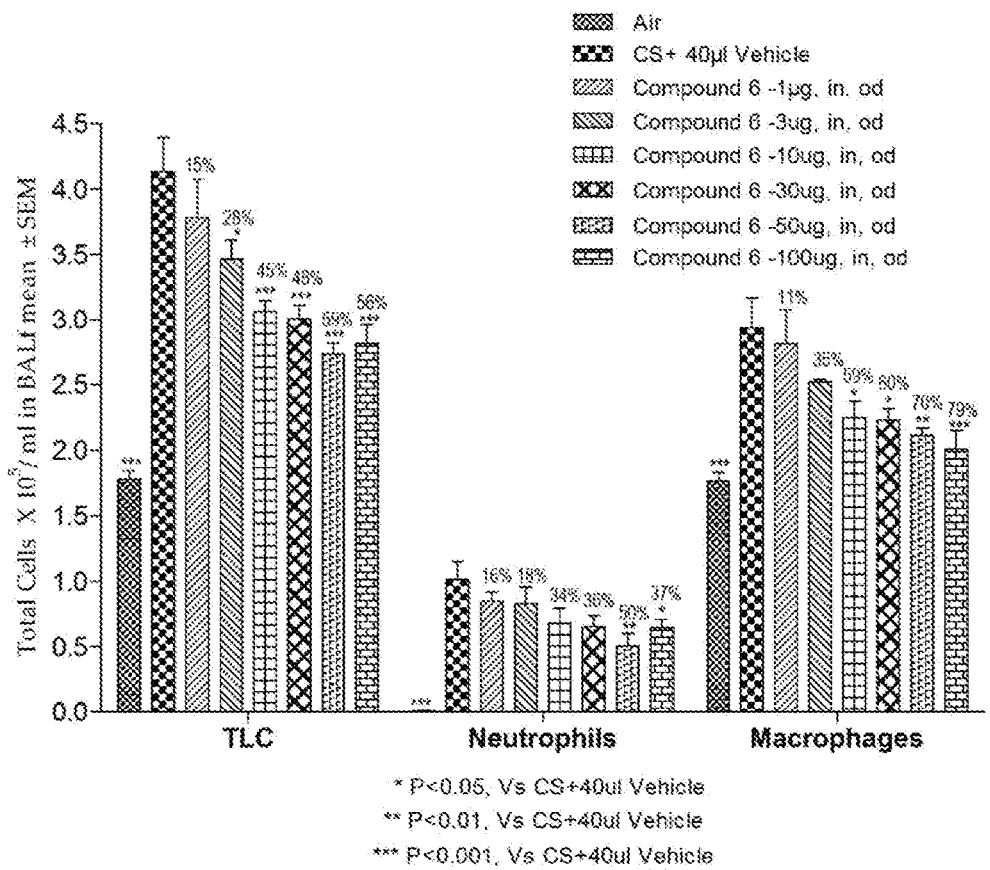
Figure 3: Effect of treatment of Compound 6 on inflammation in BALf of the animals exposed to cigarette smoke
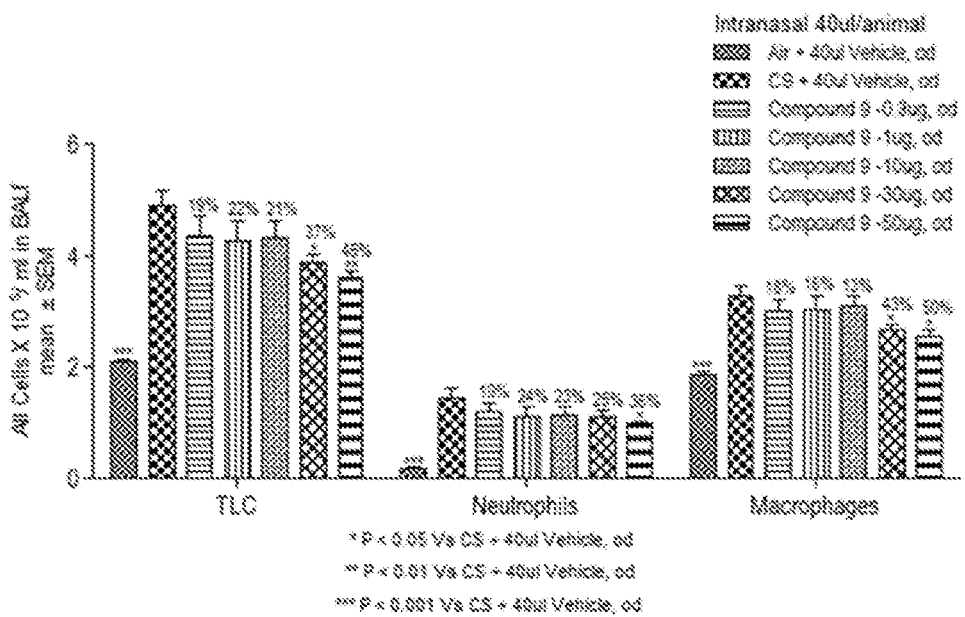
Figure 4: Effect of treatment of Compound 9 on inflammation in BALf of the animals exposed to cigarette smoke

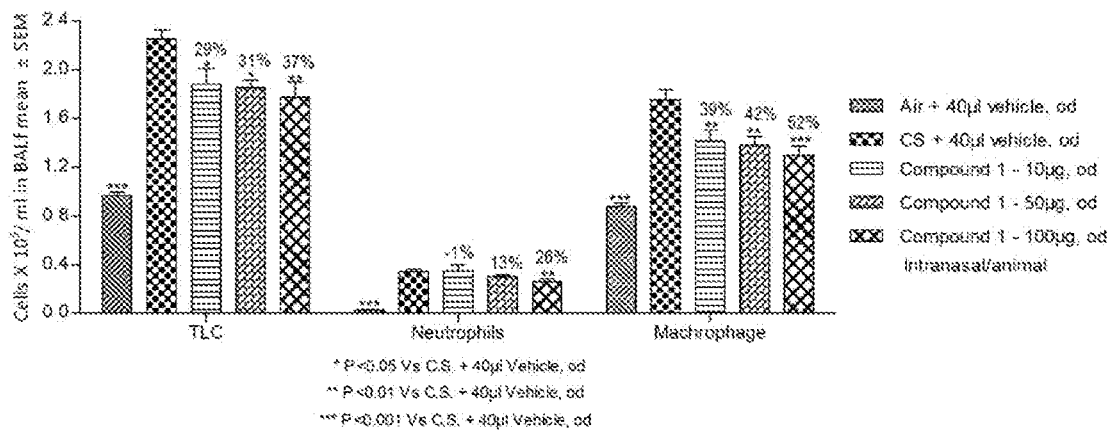
Figure 5: Effect of Compound 1 treatment on inflammation in BALf of the animals chronically exposed to CS
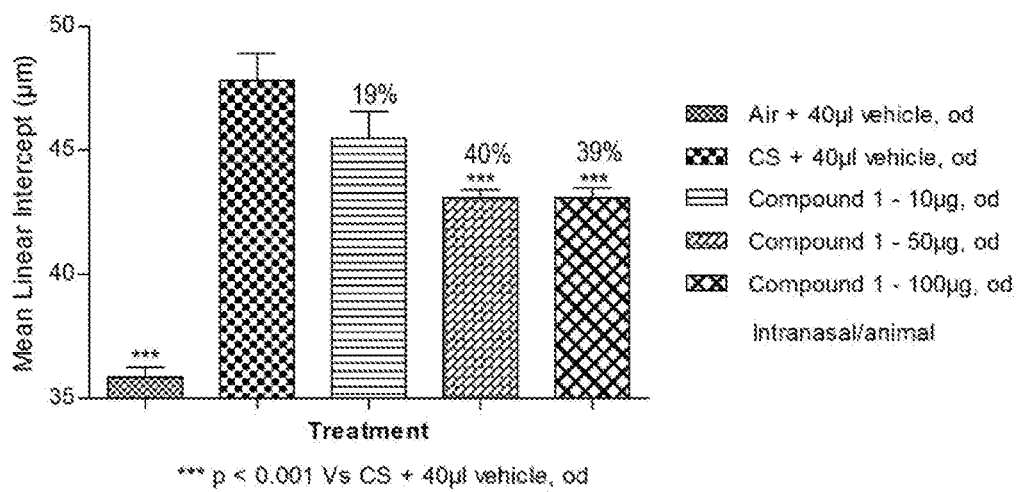
Figure 6: Effect of Compound 1 treatment on emphysema in BALf of the animals chronically exposed to CS

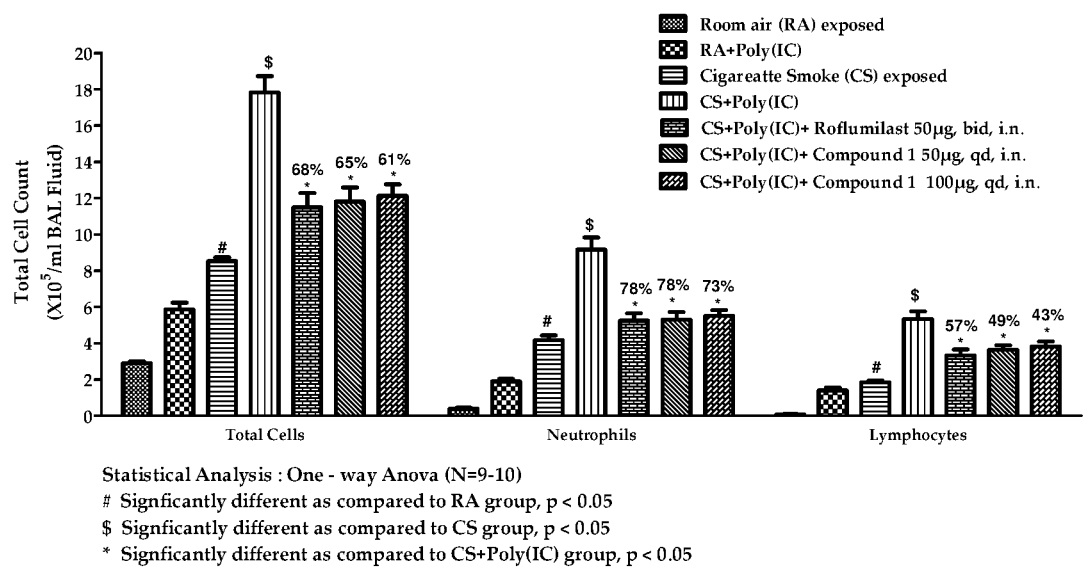
Figure 7: Efficacy of Compound 1 on Poly (I:C) induced COPD exacerbation in female C57BL/6 mice

TREATMENT OF RESPIRATORY DISORDERS USING ROR-GAMMA INHIBITORS

RELATED APPLICATIONS

This application claims the benefit of Indian Provisional Application Nos. 2091/MUM/2015 filed on May 29, 2015; and 201621011426 filed on Mar. 31, 2016, each of which is hereby incorporated by reference in its entirety.

TECHNICAL FIELD

The present patent application relates to treatment of a respiratory disorder in a subject using retinoid-related orphan receptor gamma t (ROR-gamma) inhibitors. Particularly, the present patent application relates to treatment of a respiratory disorder in a subject using a RORγ inhibitor, wherein the RORγ inhibitor is administered by an inhalation route to the subject in need thereof.

BACKGROUND

Retinoid-related orphan receptors (RORs) are transcription factors which belong to the steroid hormone nuclear receptor super family. The ROR family consists of three members, ROR alpha (RORα), ROR beta (RORβ) and ROR gamma (RORγ), also known as NR1F1, NR1F2 and NR1F3 respectively (and each encoded by a separate gene RORA, RORB and RORC, respectively). RORs contain four principal domains shared by the majority of nuclear receptors: an N-terminal A/B domain, a DNA-binding domain, a hinge domain, and a ligand binding domain. Each ROR gene generates several isoforms which differ only in their N-terminal A/B domain. Two isoforms of RORγ, RORγ1 and RORγt (also known as RORγ2) have been identified.

RORγt is a truncated form of RORγ, lacking the first N-terminal 21 amino acids and is exclusively expressed in cells of the lymphoid lineage and embryonic lymphoid tissue inducers (Sun et al., *Science,* 2000, 288, 2369-2372; Eberl et al., *Nat Immunol.,* 2004, 5: 64-73) in contrast to RORγ which is expressed in multiple tissues (heart, brain, kidney, lung, liver and muscle).

RORγt has been identified as a key regulator of Th17 cell differentiation. Th17 cells are a subset of T helper cells which produce IL-17 and other proinflammatory cytokines and have been shown to have key functions in several mouse autoimmune disease models including experimental autoimmune encephalomyelitis (EAE) and collagen-induced arthritis (CIA). In addition, Th17 cells have also been associated in the pathology of a variety of human inflammatory and autoimmune disorders including multiple sclerosis, rheumatoid arthritis, psoriasis, Crohn's disease and asthma (Jetten et al., *Nucl. Recept. Signal,* 2009, 7:e003; Manel et al., *Nat. Immunol.,* 2008, 9, 641-649). The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (Steinman et al., *J. Exp. Med.,* 2008, 205: 1517-1522; Leung et al., *Cell. Mol. Immunol.,* 2010 7: 182-189). Th17 cells are activated during the disease process and are responsible for recruiting other inflammatory cells types, especially neutrophils, to mediate pathology in the target tissues (Korn et al., *Annu. Rev. Immunol.,* 2009, 27:485-517) and RORγt has been shown to play a critical role in the pathogenic responses of Th17 cells (Ivanov et al., *Cell,* 2006 126: 1121-1133). RORγ t deficient mice have shown no Th17 cells and also resulted in amelioration of EAE. The genetic disruption of RORγ in a mouse colitis model also prevented colitis development (Buonocore et al., *Nature,* 2010, 464: 1371-1375). The role of RORγt in the pathogenesis of autoimmune or inflammatory diseases has been well documented in the literature. (Jetten et al., *Adv. Dev. Biol.,* 2006, 16:313-355; Meier et al. *Immunity,* 2007, 26:643-654; Aloisi et al., *Nat. Rev. Immunol.,* 2006, 6:205-217; Jager et al., *J. Immunol.,* 2009, 183:7169-7177; Serafmi et al., *Brain Pathol.,* 2004, 14: 164-174; Magliozzi et al., *Brain,* 2007, 130: 1089-1104; Barnes et al., *Nat. Rev. Immunol.,* 2008, 8: 183-192).

In addition, RORγt has also been shown to play a crucial role in other non-Th17 cells, such as mast cells (Hueber et al., *J Immunol.,* 2010, 184: 3336-3340). RORγt expression and secretion of Th17-type of cytokines has also been reported in NK T-cells (Eberl et al., *Nat. Immunol.,* 2004, 5: 64-73) and gamma-delta T-cells (Sutton et al, *Nat. Immunol.,* 2009, 31: 331-341; Louten et al., *J Allergy Clin. Immunol.,* 2009, 123: 1004-1011), suggesting an important function for RORγt in these cells.

Respiratory disorders related to airway inflammation include a number of severe lung diseases including asthma and COPD (Chronic Obstructive Pulmonary Diseases). The airways of asthmatic patients are infiltrated by inflammatory leukocytes, of which the eosinophil is believed to be the most prominent component. Inflammatory sensitization of airway neurons is believed to increase nasal sensitivity, heighten the sense of irritation, and promote fluid secretion, airway narrowing, and bronchoconstriction. Oxidative stress is a hallmark of most acute and chronic inflammatory airway conditions, including viral infections, asthma, rhinitis, and COPD.

Asthma and COPD are major chronic diseases related to airway obstruction. The Global Initiative for Chronic Obstructive Lung Disease provides guidelines for the distinction between asthma and COPD. Asthma is believed to be a chronic inflammatory disease wherein the airflow limitation is more or less reversible while it is more or less irreversible in the case of COPD. Asthma among other things is believed to be triggered by inhalation of sensitizing agents (like allergens) unlike noxious agents (like particles and certain gases) in the case of COPD. Though both are believed to have an inflammatory component, the inflammation in asthma is believed to be mostly eosinophilic and CD-4 driven, while it is believed to be mostly neutrophilic and CD-8 driven in COPD. Emphysema is a type of COPD in which tiny air sacs in the lungs—alveoli—fill up with air. As the air continues to build up in these sacs, they expand, and may break or become damaged and form scar tissue. The patient becomes progressively short of breath.

PCT Publication Nos. WO 2012/139775, WO 2012/027965, WO 2012/028100, WO 2012/100732, WO 2012/100734, WO2012/064744 and WO 2013/171729 disclose heterocyclic compounds which are modulators of retinoid-related orphan receptor gamma (RORγ) receptor activity.

We have surprisingly found that RORγ inhibitors, which have high potency (e.g., $IC_{50}$ for inhibiting human RORγ receptor activity of less than 2 micromolar) are effective in the treatment of respiratory disorders when administered to a subject by an inhalation route, for example, by in-mouth or intranasal administration.

SUMMARY

The present invention relates to treatment of a respiratory disorder in a subject using a RORγ inhibitor. In an embodiment the RORγ inhibitor is administered by an inhalation route to the subject in need thereof.

Thus, in an embodiment, the present invention relates to a method of treating a respiratory disorder in a subject, said method comprising administering to the subject an effective amount of a RORγ inhibitor. It is specifically contemplated that the inhibition of human RORγ receptor activity is the principal, but not the exclusive, therapeutic mode of action of the RORγ inhibitor.

In another embodiment, the present invention relates to a method of treating a respiratory disorder in a subject, said method comprising administering to the subject by an inhalation route an effective amount of a RORγ inhibitor having an $IC_{50}$ for inhibiting human RORγ receptor activity of less than 2 micromolar. In a preferred embodiment, the RORγ inhibitor has an $IC_{50}$ for inhibiting human RORγ receptor activity of less than 1 micromolar, or less than 700 nanomolar or more preferably, less than 500 nanomolar.

Thus, in an embodiment, the present invention relates to a method of treating a respiratory disorder in a subject, said method comprising administering to the subject by intranasal route an effective amount of a RORγ inhibitor having an $IC_{50}$ for inhibiting human RORγ receptor activity of less than 2 micromolar. In a preferred embodiment, the RORγ inhibitor has an $IC_{50}$ for inhibiting human RORγ receptor activity of less than 1 micromolar, or less than 700 nanomolar or more preferably, less than 500 nanomolar.

In a preferred embodiment, the respiratory disorder includes airway inflammation, asthma, bronchitis, lung emphysema or COPD. More preferably, the respiratory disorder is asthma or COPD.

In an embodiment, the present invention relates to the treatment of diseases mediated by IL-17 blockade by using a RORγ inhibitor wherein the disorder is preferably COPD or lung emphysema.

Particularly contemplated in one embodiment, is the administration of RORγ inhibitors having high potency (e.g., an $IC_{50}$ for inhibiting human RORγ receptor activity of less than 2 micromolar), via an inhalation route for the treatment of asthma or COPD, both of which are separately contemplated.

In the context of present invention, the inhalation route comprises intranasal or oral inhalation or both, particularly wherein the RORγ inhibitor is administered to the lungs or pulmonary region of the subject.

The present invention also provides a pharmaceutical composition for inhalation administration comprising a RORγ inhibitor having an $IC_{50}$ for inhibiting human RORγ receptor activity of less than 2 micromolar, or less than 1 micromolar, or preferably less than 700 nanomolar, or more preferably less than 500 nanomolar. Pharmaceutical compositions suitable for administration by the inhalation route include oral and nasal inhalation formulations such as dry powder inhaler (DPI) formulations, metered dose inhaler (MDI) formulations (including oral and nasal aerosols), nasal sprays, and formulations suitable for nebulization.

The present invention also relates to a method of treating COPD in a subject, said method comprising administering to the subject an effective amount of a RORγ inhibitor.

In another embodiment, the present invention relates to a method of treating COPD using a RORγ inhibitor, wherein the RORγ inhibitor is administered by an inhalation route to a subject in need thereof. In this embodiment, the inhalation route comprises intranasal or oral inhalation or both, particularly wherein the RORγ inhibitor is administered to the lungs or pulmonary region of the subject.

In an embodiment, the present invention relates to a method of treating COPD in a subject, said method comprising administering to the subject an effective amount of a RORγ inhibitor by an inhalation route.

In yet another embodiment, the present invention relates to a method of treating COPD using a RORγ inhibitor, said method comprising administering to the subject an effective amount of a RORγ inhibitor having an $IC_{50}$ value for inhibiting human RORγ receptor activity of less than 2 micromolar. In a preferred embodiment, the RORγ inhibitor has an $IC_{50}$ value for inhibiting human RORγ receptor activity of less than 1 micromolar, or less than 700 nanomolar or more preferably, less than 500 nanomolar.

In yet another embodiment, the present invention relates to a method of treating COPD in a subject, said method comprising administering to the subject an effective amount of a RORγ inhibitor, wherein the RORγ inhibitor is Compound 1, structurally represented as Compound 1

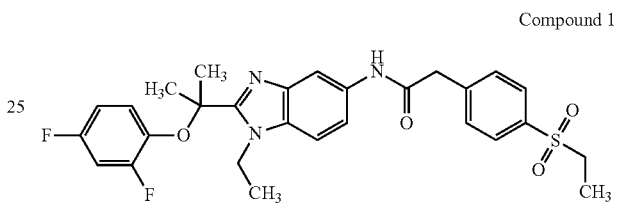

or a pharmaceutically acceptable salt thereof. In this embodiment, the RORγ inhibitor is administered to the subject by an inhalation route.

In yet another embodiment, the present invention relates to a method of treating COPD in a subject, said method comprising administering to the subject an effective amount of a RORγ inhibitor by an inhalation route, wherein the RORγ inhibitor is Compound 1, structurally represented as Compound 1

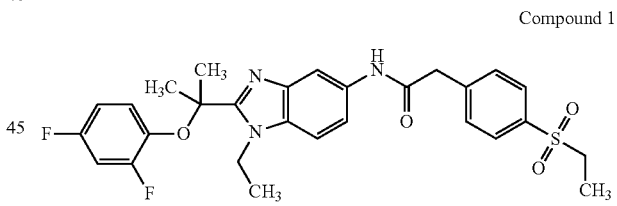

or a pharmaceutically acceptable salt thereof.

In yet another embodiment, the present invention relates to a method of treating COPD in a subject, said method comprising administering to the subject an effective amount of a RORγ inhibitor, wherein the RORγ inhibitor is Compound 9, structurally represented as Compound 9

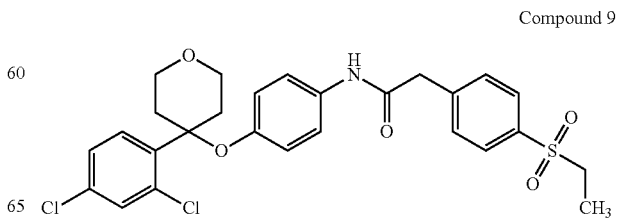

or a pharmaceutically acceptable salt thereof. In this embodiment, the RORγ inhibitor is administered to the subject by an inhalation route.

In yet another embodiment, the present invention relates to a method of treating COPD in a subject, said method comprising administering to the subject an effective amount of a RORγ inhibitor by an inhalation route, wherein the RORγ inhibitor is Compound 9, structurally represented as Compound 9 or a pharmaceutically acceptable salt thereof.

In another embodiment, the present invention relates to a method of treating COPD using a RORγ inhibitor, wherein RORγ inhibitor activity is measured by its ability to block IL-17. In this embodiment, the RORγ inhibitor is Compound 1, structurally represented as Compound 1 or a pharmaceutically acceptable salt thereof. In another embodiment, the RORγ inhibitor is Compound 9, structurally represented as Compound 9 or a pharmaceutically acceptable salt thereof.

In yet another embodiment, the present invention relates to a method of treating COPD by reducing the leukocyte count in a subject, said method comprising administering to the subject an effective amount of a RORγ inhibitor. In this embodiment the RORγ inhibitor is administered to the subject by an inhalation route.

In yet another embodiment, the present invention relates to a method of treating COPD by reducing the leukocyte count in a subject, said method comprising administering to the subject an effective amount of a RORγ inhibitor by an inhalation route, wherein the RORγ inhibitor is Compound 1, structurally represented as Compound 1 or a pharmaceutically acceptable salt thereof.

In yet another embodiment, the present invention relates to a method of treating COPD by reducing the leukocyte count in a subject, said method comprising administering to the subject an effective amount of a RORγ inhibitor by an inhalation route, wherein the RORγ inhibitor is Compound 9, structurally represented as Compound 9 or a pharmaceutically acceptable salt thereof.

In yet another embodiment, the present invention relates to a method of treating COPD by reducing the neutrophil count in a subject, said method comprising administering to the subject an effective amount of a RORγ inhibitor. In this embodiment the RORγ inhibitor is administered to the subject by an inhalation route.

In yet another embodiment, the present invention relates to a method of treating COPD by reducing the neutrophil count in a subject, said method comprising administering to the subject an effective amount of a RORγ inhibitor by an inhalation route, wherein the RORγ inhibitor is Compound 1, structurally represented as Compound 1 or a pharmaceutically acceptable salt thereof.

In yet another embodiment, the present invention relates to a method of treating COPD by reducing the neutrophil count in a subject, said method comprising administering to the subject an effective amount of a RORγ inhibitor by an inhalation route, wherein the RORγ inhibitor is Compound 9, structurally represented as Compound 9

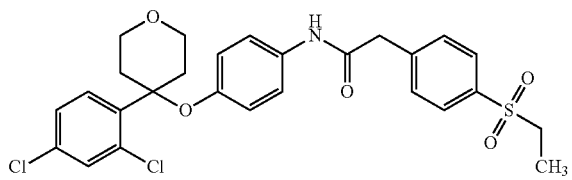

or a pharmaceutically acceptable salt thereof.

In yet another embodiment, the present invention relates to a method of treating COPD by reducing the macrophages count in a subject, said method comprising administering to the subject an effective amount of a RORγ inhibitor. In this embodiment the RORγ inhibitor is administered to the subject by an inhalation route.

In yet another embodiment, the present invention relates to a method of treating COPD by reducing the macrophages count in a subject, said method comprising administering to the subject an effective amount of a RORγ inhibitor by an inhalation route, wherein the RORγ inhibitor is Compound 1, structurally represented as Compound 1

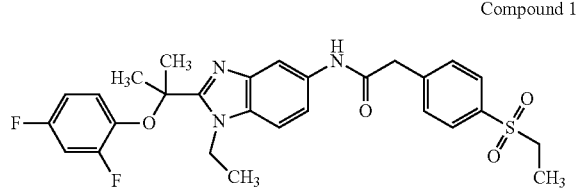 [SMILES: CCn1c(C(C)(C)Oc2ccc(F)cc2F)nc2cc(NC(=O)Cc3ccc(S(=O)(=O)CC)cc3)ccc21]

or a pharmaceutically acceptable salt thereof.

In yet another embodiment, the present invention relates to a method of treating COPD by reducing the macrophages count in a subject, said method comprising administering to the subject an effective amount of a RORγ inhibitor by an inhalation route, wherein the RORγ inhibitor is Compound 9, structurally represented as Compound 9

or a pharmaceutically acceptable salt thereof.

In yet another embodiment, the present invention relates to a method of treating COPD by reducing the leukocyte or neutrophil or macrophages count or all three in a subject, said method comprising administering to the subject an effective amount of a RORγ inhibitor. In this embodiment the RORγ inhibitor is administered to the subject by an inhalation route.

In yet another embodiment, the present invention relates to a method of treating COPD by reducing the leukocyte or neutrophil or macrophages count or all three in a subject, said method comprising administering to the subject an effective amount of a RORγ inhibitor by an inhalation route, wherein the RORγ inhibitor is Compound 1, structurally represented as Compound 1

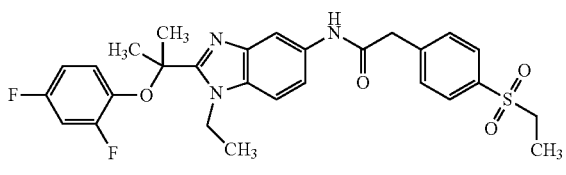

or a pharmaceutically acceptable salt thereof.

In yet another embodiment, the present invention relates to a method of treating COPD by reducing the leukocyte or neutrophil or macrophages count or all three in a subject, said method comprising administering to the subject an effective amount of a RORγ inhibitor by an inhalation route, wherein the RORγ inhibitor is Compound 1, structurally represented as Compound 9

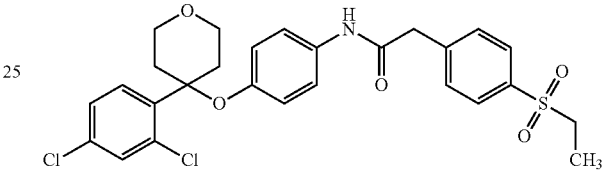

or a pharmaceutically acceptable salt thereof.

The present invention relates to a method of identifying a RORγ inhibitor useful for treating a respiratory disorder by an inhalation administration in a subject, said method comprising:
   (a) determining an $IC_{50}$ for inhibiting human RORγ receptor activity of each of a plurality of compounds;
   (b) selecting the compounds having an $IC_{50}$ for inhibiting human RORγ receptor activity of less than 2 micromolar;
   (c) evaluating the in vivo activity of the identified compounds in a respiratory disorder model assay, wherein the compounds are administered by the inhalation route; and
   (d) identifying the compounds to be effective for treating the respiratory disorder.

In an embodiment, the respiratory disorder is COPD.

The present invention, in an embodiment, provides use of an effective amount of a RORγ inhibitor in the manufacture of a composition for the treatment of COPD in a subject in need thereof.

The present invention, in another embodiment, provides use of an effective amount of a RORγ inhibitor in the manufacture of a composition for inhalation administration for the treatment of COPD in a subject in need thereof.

In yet another embodiment, the present invention relates to use of an effective amount of a RORγ inhibitor in the manufacture of a composition for inhalation administration for the treatment of COPD in a subject by reducing the leukocyte or neutrophil or macrophages count or all three in a subject in need thereof.

In another embodiment, the present invention relates to use of an effective amount of compound 1 or a pharmaceutically acceptable salt thereof as a RORγ inhibitor in the manufacture of a composition for the treatment of COPD in a subject.

In yet another embodiment, the present invention relates to use of an effective amount of compound 1 or a pharmaceutically acceptable salt thereof as a RORγ inhibitor in the manufacture of a composition suitable for inhalation administration for the treatment of COPD in a subject.

In another embodiment, the present invention relates to use of an effective amount of compound 9 or a pharmaceutically acceptable salt thereof as a RORγ inhibitor in the manufacture of a composition for the treatment of COPD in a subject.

In yet another embodiment, the present invention relates to use of an effective amount of compound 9 or a pharmaceutically acceptable salt thereof as a RORγ inhibitor in the manufacture of a composition suitable for inhalation administration for the treatment of COPD in a subject.

In yet another embodiment, the present invention relates to use of a RORγ inhibitor in the dosage range from about 0.1 mcg/kg to about 30 mg/kg in the manufacture of a composition for inhalation administration for the treatment of COPD in a subject in need thereof.

In yet another embodiment, the present invention relates to use of a RORγ inhibitor in the dosage range from about 0.1 mcg/kg to about 30 mg/kg in the manufacture of a composition for inhalation administration for the treatment of COPD in a subject in need thereof by reducing the leukocyte or neutrophil or macrophages count or all three in a subject in need thereof.

In an embodiment, the present invention relates to use of an effective amount of compound 1 as a RORγ inhibitor in the manufacture of a composition for inhalation administration for the treatment of COPD in a subject.

In another embodiment, the present invention relates to use of compound 1 or a pharmaceutically acceptable salt thereof as a RORγ inhibitor in the dosage range from about 0.1 mcg/kg to about 30 mg/kg in the manufacture of a composition by inhalation administration for the treatment of COPD in a subject in need thereof.

In another embodiment, the present invention relates to use of compound 1 or a pharmaceutically acceptable salt thereof as a RORγ inhibitor in the dosage range from about 0.1 mcg/kg to about 30 mg/kg in the manufacture of a composition for inhalation administration for the treatment of COPD in a subject in need thereof by reducing the leukocyte or neutrophil or macrophages count or all three in a subject in need thereof.

In an embodiment, the present invention relates to use of an effective amount of compound 9 or a pharmaceutically acceptable salt thereof as a RORγ inhibitor in the manufacture of a composition for inhalation administration for the treatment of COPD in a subject.

In another embodiment, the present invention relates to use of an effective amount of compound 9 or a pharmaceutically acceptable salt thereof as a RORγ inhibitor in the manufacture of a composition for inhalation administration for the treatment of COPD in a subject by reducing the leukocyte or neutrophil or macrophages count or all three in a subject in need thereof.

In another embodiment, the present invention relates to use of compound 9 or a pharmaceutically acceptable salt thereof as a RORγ inhibitor in the dosage range from about 0.1 mcg/kg to about 30 mg/kg in the manufacture of a composition for inhalation administration for the treatment of COPD in a subject in need thereof.

In another embodiment, the present invention relates to use of compound 9 or a pharmaceutically acceptable salt thereof as a RORγ inhibitor in the dosage range from about 0.1 mcg/kg to about 30 mg/kg in the manufacture of a composition for inhalation administration for the treatment of COPD in a subject in need thereof by reducing the leukocyte or neutrophil or macrophages count or all three in a subject in need thereof.

The present invention, in an embodiment, also provides use of an effective amount of a RORγ inhibitor having an $IC_{50}$ for inhibiting human RORγ receptor activity of less than 2 micromolar in the manufacture of a composition for inhalation administration for the treatment of COPD in a subject. Preferably, the RORγ inhibitor has an $IC_{50}$ for inhibiting human RORγ receptor activity of less than 1 micromolar or less than 700 nanomolar, or more preferably, less than 500 nanomolar.

In another embodiment, the present invention provides use of an effective amount of a RORγ inhibitor having an $IC_{50}$ for inhibiting human RORγ receptor activity of less than 2 micromolar in the manufacture of a composition for inhalation administration for the treatment of COPD in a subject, wherein such inhibition of human RORγ receptor activity is the principal therapeutic mode of action of the RORγ inhibitor.

In an aspect, the RORγ inhibitor useful in the context of this invention is selected from one of the following formula (A) or formula (B)

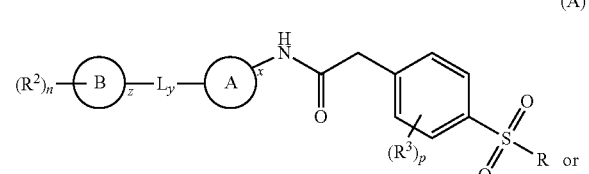

(A)

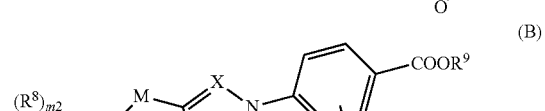

or (B)

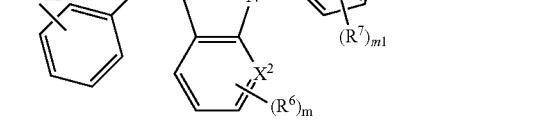

or a pharmaceutically acceptable salt thereof
wherein, in formula (A)
Ring A is

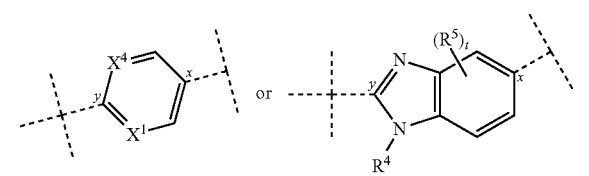

$X^1$ and $X^4$, which may be same or different, are each independently selected from N, CH and $CR^1$;

Ring B is selected from phenyl, pyridinyl, benzimidazolyl, indolyl, [1,2,4]triazolo[4,3-a]pyridinyl and [1,2,4]oxadiazolyl;

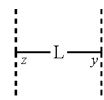

is selected from

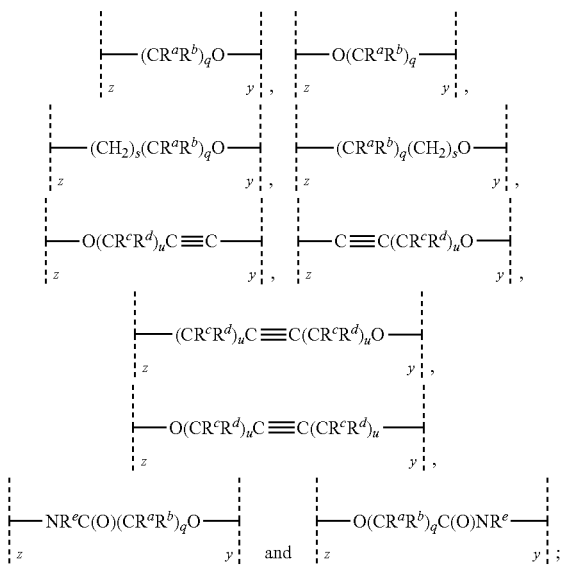

x, y and z each represent a point of attachment;
R is selected from $C_{1-8}$alkyl and halo$C_{1-8}$alkyl;
each occurrence of $R^1$ is independently selected from halogen, cyano, hydroxyl and $C_{1-8}$alkyl;
each occurrence of $R^2$ is independently selected from halogen, cyano, hydroxyl, $C_{1-8}$alkyl, $C_{1-8}$alkoxy, halo$C_{1-8}$alkyl, halo$C_{1-8}$alkoxy, hydroxy$C_{1-8}$alkyl, $C_{3-6}$cycloalkyl, $C_{3-6}$cycloalkyl$C_{1-8}$alkyl and 4-chloro-phenyl;
each occurrence of $R^3$ is independently selected from halogen, cyano, hydroxyl and $C_{1-4}$alkyl;
$R^4$ is selected from hydrogen, —$(CH_2)_2N(CH_3)_2$, $C_{1-8}$alkyl, halo$C_{1-8}$alkyl, $C_{3-6}$cycloalkyl and $C_{3-6}$cycloalkyl$C_{1-8}$alkyl;
each occurrence of $R^5$ is independently selected from halogen, cyano, hydroxyl and $C_{1-8}$alkyl;
each occurrence of $R^a$ and $R^b$, which may be same or different, are each independently selected from halogen, $C_{1-8}$alkyl, halo$C_{1-8}$alkyl and $C_{1-8}$alkoxy; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;
each occurrence of $R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;
$R^e$ is selected from $C_{1-8}$alkyl, halo$C_{1-8}$alkyl and $C_{3-6}$cycloalkyl;
'n' is 0, 1, 2 or 3;
'p' is 0, 1 or 2;
'q' is 1 or 2;
's' is 1, 2 or 3;
't' is 0, 1 or 2; and
'u' is 1 or 2;
and in formula (B)
M is selected from —O— and —C(O)—;
X is selected from N and CH;
$X^2$ is selected from N and CH;
each occurrence of $R^6$ is independently selected from halogen, hydroxyl and —$CON(CH_3)_2$;

each occurrence of $R^7$ is independently selected from halogen and hydroxyl;
each occurrence of $R^8$ is independently selected from halogen, $C_{1-8}$alkyl, halo$C_{1-8}$alkyl and $C_{3-6}$cycloalkyl;
$R^9$ is selected from hydrogen and $C_{1-4}$alkyl;
'm' is 0, 1, 2 or 3;
'$m_1$' is 0, 1, 2 or 3; and
'$m_2$' is 0, 1, 2, 3 or 4.

In an embodiment, the RORγ inhibitor useful in the context of this invention is selected from one of the following formula (A-1), formula (A-2) or formula (B-1)

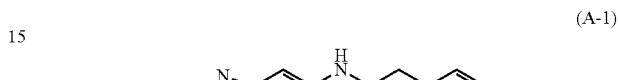
(A-1)

(A-2)

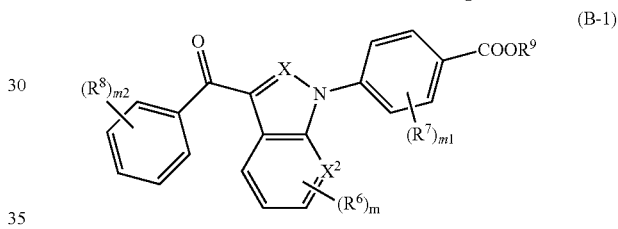
(B-1)

or a pharmaceutically acceptable salt thereof,
wherein, in formulae (A-1) and (A-2)
$X^1$ is selected from N, CH and $CR^1$;
Ring B is selected from phenyl, pyridinyl, benzimidazolyl, indolyl, [1,2,4]triazolo[4,3-a]pyridinyl and [1,2,4]oxadiazolyl;

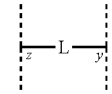

is selected from

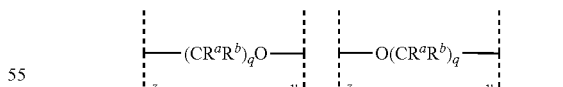

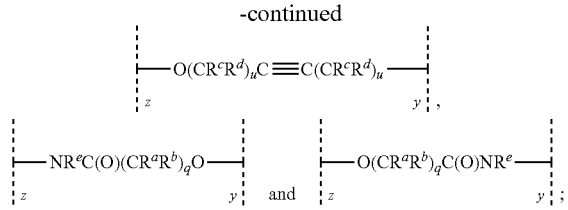

y and z represents point of attachment;

R¹ is independently selected from halogen, cyano, hydroxyl and $C_{1-8}$alkyl;

each occurrence of R² is independently selected from halogen, cyano, hydroxyl, $C_{1-8}$alkyl, $C_{1-8}$alkoxy, halo$C_{1-8}$alkyl, halo$C_{1-8}$alkoxy, hydroxy$C_{1-8}$alkyl, $C_{3-6}$cycloalkyl, $C_{3-6}$cycloalkyl$C_{1-8}$alkyl and 4-chloro-phenyl;

R⁴ is selected from hydrogen, —(CH₂)₂N(CH₃)₂, $C_{1-8}$alkyl, halo$C_{1-8}$alkyl, $C_{3-6}$cycloalkyl and $C_{3-6}$cycloalkyl$C_{1-8}$alkyl;

each occurrence of $R^a$ and $R^b$, which may be same or different, are each independently selected from halogen, $C_{1-8}$alkyl, halo$C_{1-8}$alkyl and $C_{1-8}$alkoxy; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;

each occurrence of $R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;

$R^e$ is selected from $C_{1-8}$alkyl, halo$C_{1-8}$alkyl and $C_{3-6}$cycloalkyl;

'n' is 0, 1, 2 or 3;

'q' is 1 or 2;

's' is 1, 2 or 3; and

'u' is 1;

and in formula (B-1)

X is selected from N and CH;

X² is selected from N and CH;

each occurrence of R⁶ is independently selected from halogen, hydroxyl and —CON(CH₃)₂;

each occurrence of R⁷ is independently selected from halogen and hydroxyl;

each occurrence of R⁸ is independently selected from halogen, $C_{1-8}$alkyl, halo$C_{1-8}$alkyl and $C_{3-6}$cycloalkyl;

R⁹ is selected from hydrogen and $C_{1-4}$alkyl;

'm' is 0, 1, 2 or 3;

'm₁' is 0, 1, 2 or 3; and

'm₂' is 0, 1, 2, 3 or 4.

In a preferred embodiment, the RORγ inhibitor useful in the context of this invention is selected from one of the compounds structurally represented below Compound 1

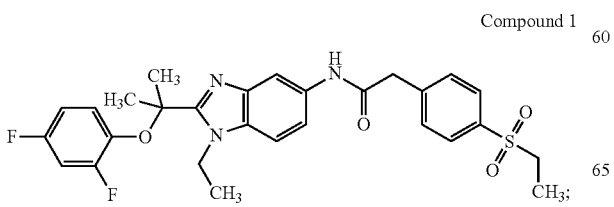

Compound 2

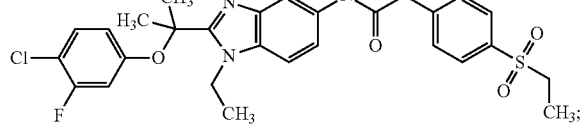

Compound 3

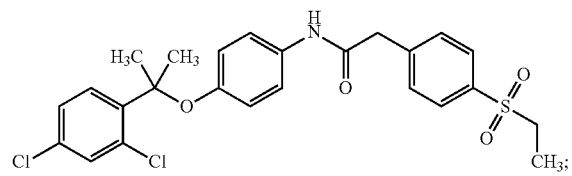

Compound 4

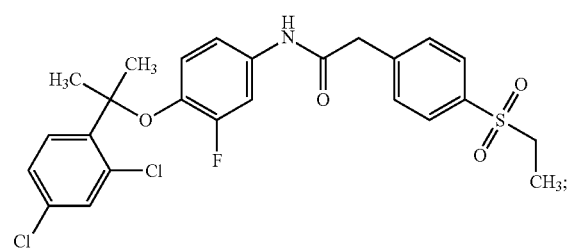

Compound 5

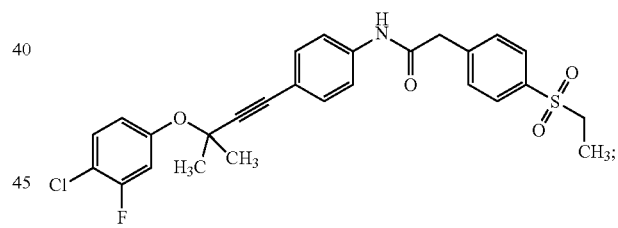

Compound 6

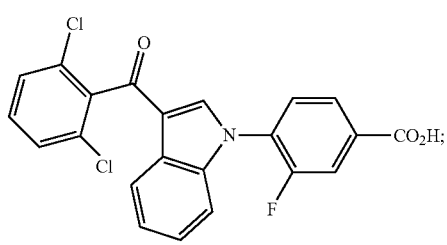

Compound 7

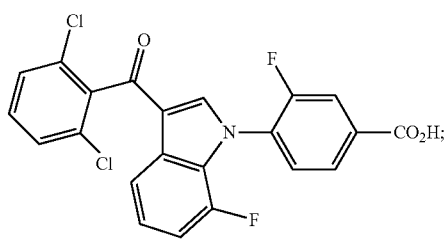

-continued

Compound 8

Compound 9

Compound 10 and

Compound 11 or a pharmaceutically acceptable salt thereof.

BRIEF DESCRIPTION OF THE DRAWINGS

FIG. 1 is a bar graph that represents the effect of treatment of Compound 1 on inflammation in BALf of the animals exposed to cigarette smoke (CS) as described in Example 2.

FIG. 2 is a bar graph that represents the effect of treatment of Compound 3 on inflammation in BALf of the animals exposed to cigarette smoke as described in Example 3.

FIG. 3 is a bar graph that represents the effect of treatment of Compound 6 on inflammation in BALf of the animals exposed to cigarette smoke as described in Example 4.

FIG. 4 is a bar graph that represents the effect of treatment of Compound 9 on inflammation in BALf of the animals exposed to cigarette smoke as described in Example 5.

FIG. 5 is a bar graph that represents the effect of Compound 1 treatment on inflammation in BALf of the animals chronically exposed to CS.

FIG. 6 is a bar graph that represents the effect of Compound 1 treatment on emphysema in BALf of the animals chronically exposed to CS.

FIG. 7 is a bar graph that represents the efficacy of Compound 1 on Poly (I:C) induced COPD exacerbation in female C57BL/6 mice.

DETAILED DESCRIPTION

The present invention relates to treatment of a respiratory disorder in a subject using a RORγ inhibitor. In an embodiment the RORγ inhibitor is administered by an inhalation route to the subject in need thereof.

The present invention relates to treatment of COPD in a subject using a RORγ inhibitor. In an embodiment the RORγ inhibitor is administered by an inhalation route to the subject in need thereof.

Definitions

The terms used herein are defined as follows. If a definition set forth in the present application and a definition set forth later in a non-provisional application claiming priority from the present provisional application are in conflict, the definition in the non-provisional application shall control the meaning of the terms.

The term "effective amount" or "therapeutically effective amount" denotes an amount of the RORγ inhibitor that, when administered to a subject by an inhalation route for treating a respiratory disorder mediated by RORγ modulation, produces or is sufficient to produce medically significant therapeutic benefit in a subject.

The term "medically significant" denotes an amount sufficient to provide at least a minimal medical benefit to the subject. The effective amount of the RORγ inhibitor as described herein can range from 0.1 mcg/kg to 30 mg/kg, to be administered by an inhalation route to the subject; although larger or smaller amounts are not excluded if they fall within the scope of the definition of this paragraph. In an embodiment, the effective amount of RORγ inhibitor to be administered per day may range from about 1 mcg to about 500 mg.

Specifically, therapeutically effective amount of Compound 1 or its pharmaceutically acceptable salt may range from about 0.1 mcg/kg to about 30 mg/kg. The therapeutically effective amount of Compound 1 or its pharmaceutically acceptable salt to be administered per day encompasses a dose from about 1 mcg to about 2 gm. The therapeutically effective amount of Compound 9 or its pharmaceutically acceptable salt may range from about 0.1 mcg/kg to about 30 mg/kg. The therapeutically effective amount of Compound 9 or its pharmaceutically acceptable salt to be administered per day encompasses a dose from about 1 mcg to about 2 gm.

The term "compound" (used interchangeably with "agent" or "inhibitor") includes both chemical molecules, for example, small organic molecules and biological molecules, for example, protein antibodies. It also includes its tautomers, stereoisomers, enantiomers, and diastereomers.

The term "subject" includes mammals such as humans and other animals, such as domestic animals (e.g., household pets including cats and dogs) and non-domestic animals (such as wildlife).

The term "treating" or "treatment", as used herein, is an approach for obtaining beneficial or desired results, including clinical results. For purposes of this invention, beneficial or desired clinical results include alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable.

By the term "respiratory disorder", it is meant any condition or disease related to respiration or the respiratory system and includes but is not limited to airway inflammation, asthma, emphysema, bronchitis, COPD, sinusitis, rhinitis, respiratory depression, reactive airways dysfunction syndrome (RADS), acute respiratory distress syndrome (ARDS), irritant induced asthma, occupational asthma, sensory hyper-reactivity, multiple chemical sensitivity, and aid in smoking cessation therapy. Preferably, the respiratory disorder is airway inflammation, asthma, emphysema, bronchitis, or COPD. More preferably, the respiratory disorder is asthma or COPD.

The term "$IC_{50}$" refers to the molar concentration of a compound that is needed to inhibit a given biological process by half.

The term "pharmaceutically acceptable salt" includes salts prepared from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of salts derived from inorganic bases include, but are not limited to, aluminum, ammonium, calcium, copper, ferric, ferrous, lithium, magnesium, manganic, mangamous, potassium, sodium, and zinc.

By "pharmaceutically acceptable excipient", it is meant any of the components of a pharmaceutical combination other than the actives and which are approved by regulatory authorities or are generally regarded as safe for human or animal use.

Compounds

The compounds useful in the methods and compositions of the present invention include the RORγ inhibitors that may be administered by an inhalation route (e.g., nasal or oral inhalation or both) to a subject. Exemplary RORγ inhibitors that are useful for inhalation administration in the present invention are given below. The compounds mentioned below defined under various formulae are a few representative compounds, and by no means limit the scope of the invention to only these compounds.

In an embodiment, the RORγ inhibitor useful in the context of this invention is selected from one of the following formula (A) or formula (B)

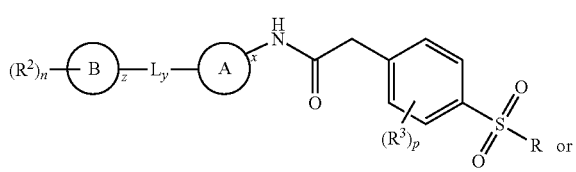
(A)

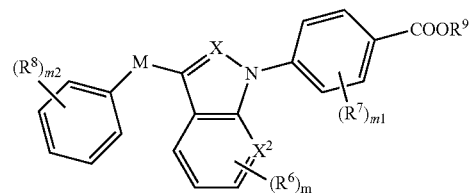
(B)

or a pharmaceutically acceptable salt thereof
wherein, in formula (A)
Ring A is

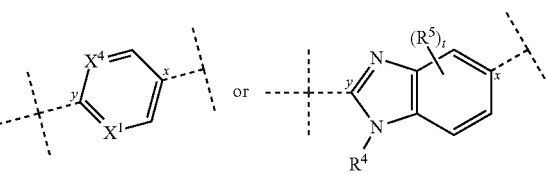

$X^1$ and $X^4$, which may be same or different, are each independently selected from N, CH and $CR^1$;

Ring B is selected from phenyl, pyridinyl, benzimidazolyl, indolyl, [1,2,4]triazolo[4,3-a]pyridinyl and [1,2,4]oxadiazolyl;

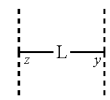

is selected from

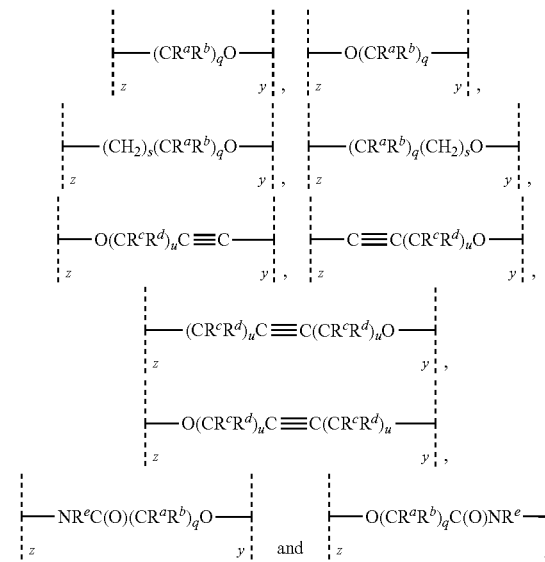

x, y and z represents point of attachment;
R is selected from $C_{1-8}$alkyl and halo$C_{1-8}$alkyl;
each occurrence of $R^1$ is independently selected from halogen, cyano, hydroxyl and $C_{1-8}$alkyl;
each occurrence of $R^2$ is independently selected from halogen, cyano, hydroxyl, $C_{1-8}$alkyl, $C_{1-8}$alkoxy, halo$C_{1-}$ salkyl, haloC$_{1-8}$alkoxy, hydroxyC$_{1-8}$alkyl, C$_{3-6}$cycloalkyl, C$_{3-6}$cycloalkylC$_{1-8}$alkyl and 4-chloro-phenyl;

each occurrence of R$^3$ is independently selected from halogen, cyano, hydroxyl and C$_{1-4}$alkyl;

R$^4$ is selected from hydrogen, —(CH$_2$)$_2$N(CH$_3$)$_2$, C$_{1-8}$alkyl, haloC$_{1-8}$alkyl, C$_{3-6}$cycloalkyl and C$_{3-6}$cycloalkylC$_{1-8}$alkyl;

each occurrence of R$^5$ is independently selected from halogen, cyano, hydroxyl and C$_{1-8}$alkyl;

each occurrence of R$^a$ and R$^b$, which may be same or different, are each independently selected from halogen, C$_{1-8}$alkyl, haloC$_{1-8}$alkyl and C$_{1-8}$alkoxy; or R$^a$ and R$^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;

each occurrence of R$^c$ and R$^d$, which may be same or different, are each independently selected from hydrogen, C$_{1-8}$alkyl, haloC$_{1-8}$alkyl and C$_{1-8}$alkoxy; or R$^c$ and R$^d$ together with the carbon atom to which they are attached, form a C$_{3-6}$cycloalkyl ring;

R$^e$ is selected from C$_{1-8}$alkyl, haloC$_{1-8}$alkyl and C$_{3-6}$cycloalkyl;

'n' is 0, 1, 2 or 3;

'p' is 0, 1 or 2;

'q' is 1 or 2;

's' is 1, 2 or 3;

't' is 0, 1 or 2; and

'u' is 1 or 2;

and in formula (B)

M is selected from —O— and —C(O)—;

X is selected from N and CH;

X$^2$ is selected from N and CH;

each occurrence of R$^6$ is independently selected from halogen, hydroxyl and —CON(CH$_3$)$_2$;

each occurrence of R$^7$ is independently selected from halogen and hydroxyl; each occurrence of R$^8$ is independently selected from halogen, C$_{1-8}$alkyl, haloC$_{1-8}$alkyl and C$_{3-6}$cycloalkyl;

R$^9$ is selected from hydrogen and C$_{1-4}$alkyl;

'm' is 0, 1, 2 or 3;

'm$_1$' is 0, 1, 2 or 3; and

'm$_2$' is 0, 1, 2, 3 or 4.

In an embodiment, ROR inhibitors useful in the context of the invention are selected from those compounds generically and specifically disclosed in PCT patent application no. PCT/IB2015/052745. Accordingly, a ROR inhibitor useful in the context of the invention has the formula (I)

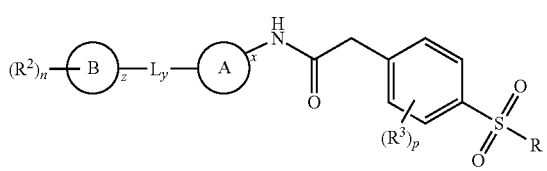

or a pharmaceutically acceptable salt thereof, wherein,
Ring A is

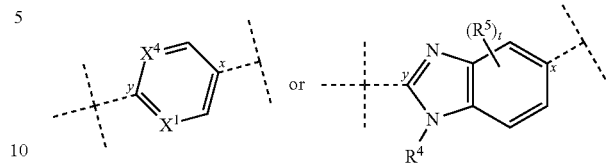

X$^1$ and X$^4$, which may be same or different, are each independently selected from N, CH and CR$^1$;

Ring B is selected from phenyl, pyridinyl, benzimidazolyl, indolyl, [1,2,4]triazolo[4,3-a]pyridinyl and [1,2,4]oxadiazolyl;

is selected from

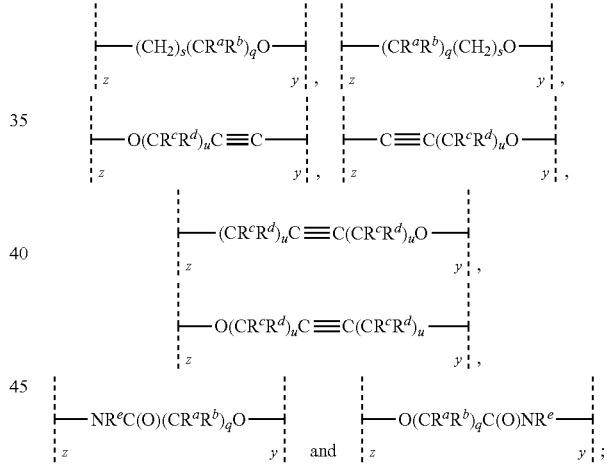

x, y and z represents point of attachment;

R is selected from C$_{1-8}$alkyl and haloC$_{1-8}$alkyl;

each occurrence of R$^1$ is independently selected from halogen, cyano, hydroxyl and C$_{1-8}$alkyl;

each occurrence of R$^2$ is independently selected from halogen, cyano, hydroxyl, C$_{1-8}$alkyl, C$_{1-8}$alkoxy, haloC$_{1-8}$alkyl, haloC$_{1-8}$alkoxy, hydroxyC$_{1-8}$alkyl, C$_{3-6}$cycloalkyl, C$_{3-6}$cycloalkylC$_{1-8}$alkyl and 4-chloro-phenyl;

each occurrence of R$^3$ is independently selected from halogen, cyano, hydroxyl and C$_{1-4}$alkyl;

R$^4$ is selected from hydrogen, —(CH$_2$)$_2$N(CH$_3$)$_2$, C$_{1-8}$alkyl, haloC$_{1-8}$alkyl, C$_{3-6}$cycloalkyl and C$_{3-6}$cycloalkylC$_{1-8}$alkyl;

each occurrence of R$^5$ is independently selected from halogen, cyano, hydroxyl and C$_{1-8}$alkyl;

each occurrence of R$^a$ and R$^b$, which may be same or different, are each independently selected from halogen, C$_{1-8}$alkyl, haloC$_{1-8}$alkyl and C$_{1-8}$alkoxy; or R$^a$ and R$^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;

each occurrence of $R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;

$R^e$ is selected from $C_{1-8}$alkyl, halo$C_{1-8}$alkyl and $C_{3-6}$cycloalkyl;

'n' is 0, 1, 2 or 3;
'p' is 0, 1 or 2;
'q' is 1 or 2;
's' is 1, 2 or 3;
't' is 0, 1 or 2; and
'u' is 1 or 2.

A few representative ROR gamma inhibitor compounds useful in the method of the invention are mentioned below:

Compound 1
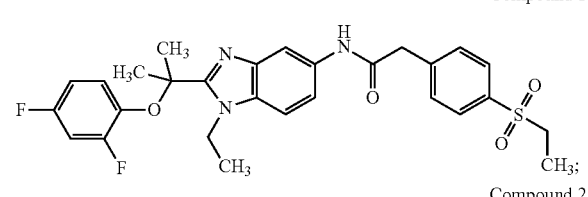

Compound 2
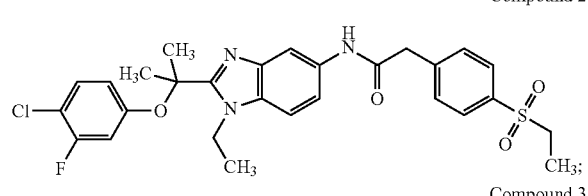

Compound 3
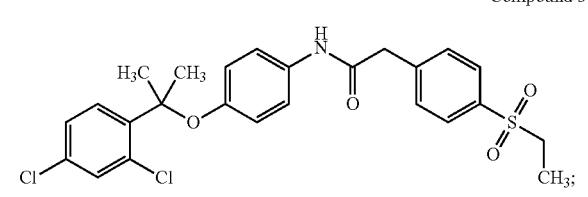

Compound 4
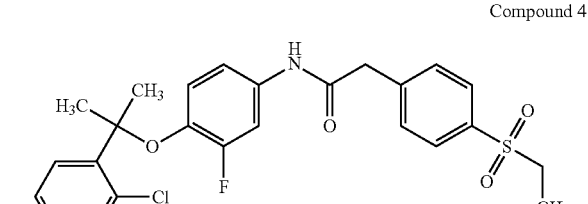

Compound 5
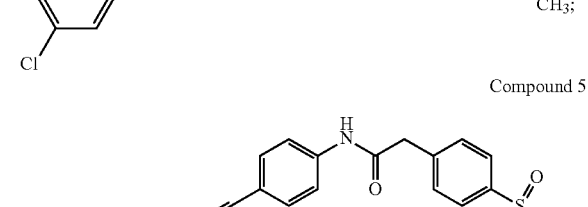

-continued

Compound 9
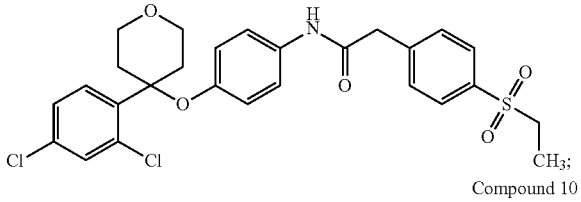

Compound 10
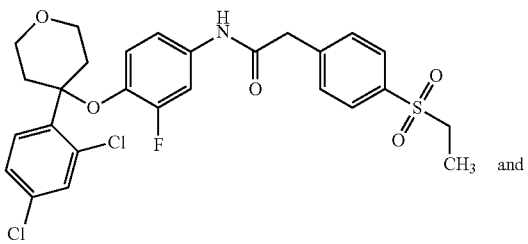
and

Compound 11
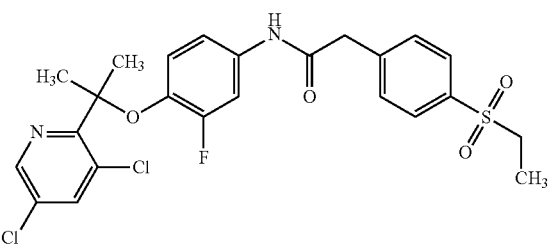

The preparation of above said compounds is disclosed in PCT patent application no. PCT/IB2015/052745.

In another embodiment, ROR inhibitors useful in the context of the invention are selected from those compounds generically and specifically disclosed in PCT patent application no. PCT/IB2014/066720. Accordingly, a ROR inhibitor useful in the context of the invention has the formula (I)

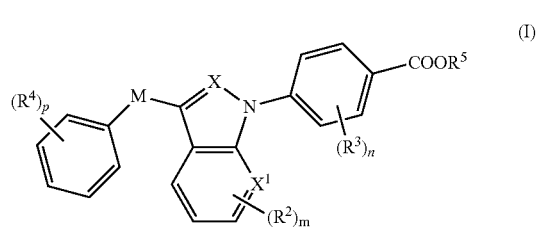

(I)

or a pharmaceutically acceptable salt thereof,
wherein,
M is selected from —O— and —C(O)—;
X is selected from N and CH;
$X^1$ is selected from N and CH;
each occurrence of $R^2$ is independently selected from halogen, hydroxyl and —CON(CH$_3$)$_2$;
each occurrence of $R^3$ is independently selected from halogen and hydroxyl;
each occurrence of $R^4$ is independently selected from halogen, $C_{1-8}$alkyl, halo$C_{1-8}$alkyl and $C_{3-6}$cycloalkyl;
$R^5$ is selected from hydrogen and $C_{1-4}$alkyl;
'm' is 0, 1, 2 or 3;
'n' is 0, 1, 2 or 3; and
'p' is 0, 1, 2, 3 or 4.

A few representative ROR gamma inhibitor compounds useful in the method of the invention are mentioned below:

Compound 6

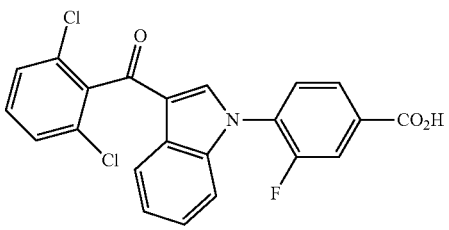

Compound 7

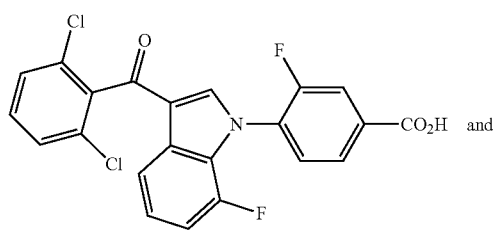

Compound 8

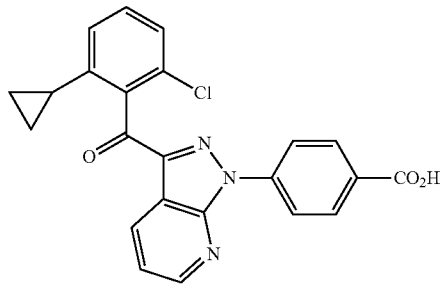

The preparation of above said compounds is disclosed in PCT patent application no. PCT/IB2014/066720.

Method of Treatment

In an embodiment, the present invention relates to a method of treating a respiratory disorder in a subject, said method comprising administering to the subject by an inhalation route an effective amount of a RORγ inhibitor having an $IC_{50}$ for inhibiting human RORγ receptor activity of less than 2 micromolar.

In another embodiment, the present invention relates to a method of treating diseases mediated by IL-17 blockade is subject in need thereof, said method comprising administering to the subject by an inhalation route an effective amount of RORγ inhibitor having an $IC_{50}$ for inhibiting human RORγ receptor activity of less than 2 micromolar.

In another embodiment, the present invention relates to a method of treating diseases mediated by IL-17 blockade is subject in need thereof, said method comprising administering to the subject by an inhalation route an effective amount of RORγ inhibitor wherein the disorder is preferably COPD or lung emphysema.

Preferably, the RORγ inhibitors used in the method of treatment in accordance with the present invention have an $IC_{50}$ for inhibiting human RORγ receptor activity of less than 1 micromolar or less than 700 nanomolar, or more preferably, less than 500 nanomolar Preferably, the RORγ inhibitors may be selected from Compound 1 and Compound 9 or a pharmaceutically acceptable salt thereof.

Thus in a specific embodiment, the present invention relates to a method of treating COPD, said method comprising administering to the subject an effective amount of a RORγ inhibitor.

In another embodiment, the present invention relates to a method of treating COPD, said method comprising administering to the subject an effective amount of a RORγ inhibitor by an inhalation route.

In yet another embodiment, the present invention relates to a method of treating COPD, said method comprising administering to the subject by an inhalation route an effective amount of a RORγ inhibitor having an $IC_{50}$ for inhibiting human RORγ receptor activity of less than 2 micromolar.

In yet another embodiment, the present invention relates to a method of treating COPD using a RORγ inhibitor, said method comprising administering to the subject an effective amount Compound 1 or a pharmaceutically acceptable salt thereof as a RORγ inhibitor wherein Compound 1 is represented by Compound 1

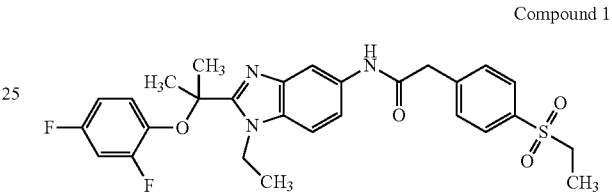

or a pharmaceutically acceptable salt thereof.

In yet another embodiment, the present invention relates to a method of treating COPD using a RORγ inhibitor, said method comprising administering to the subject by an inhalation route an effective amount Compound 1 or a pharmaceutically acceptable salt thereof as a RORγ inhibitor wherein Compound 1 is represented by Compound 1

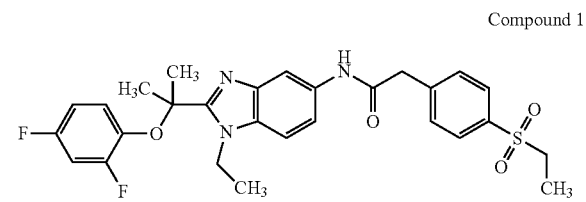 [SMILES: CCn1c(C(C)(C)Oc2ccc(F)cc2F)nc2cc(NC(=O)Cc3ccc(S(=O)(=O)CC)cc3)ccc21]

or a pharmaceutically acceptable salt thereof.

In yet another embodiment, the present invention relates to a method of treating COPD using a RORγ inhibitor, said method comprising administering to the subject an effective amount Compound 9 or a pharmaceutically acceptable salt thereof as a RORγ inhibitor wherein Compound 9 is represented by Compound 9

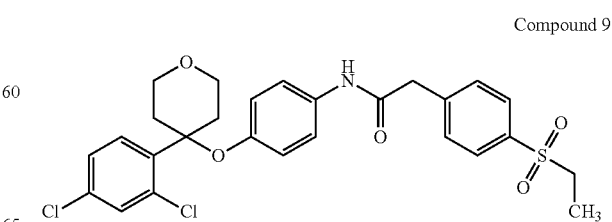

or a pharmaceutically acceptable salt thereof.

In yet another embodiment, the present invention relates to a method of treating COPD using a RORγ inhibitor, said method comprising administering to the subject by an inhalation route an effective amount Compound 9 or a pharmaceutically acceptable salt thereof as a RORγ inhibitor wherein Compound 9 is represented by Compound 9

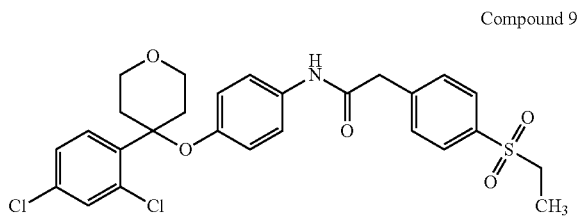 [SMILES: CCS(=O)(=O)c1ccc(CC(=O)Nc2ccc(OC3(c4ccc(Cl)cc4Cl)CCOCC3)cc2)cc1]

or a pharmaceutically acceptable salt thereof.

In yet another embodiment, the present invention relates to a method of treating COPD using a RORγ inhibitor, wherein RORγ inhibitor activity is measured by its ability to block IL-17.

In yet another embodiment, the present invention relates to a method of treating COPD by reducing the leukocyte count in a subject, said method comprising administering to the subject an effective amount of a RORγ inhibitor.

In yet another embodiment, the present invention relates to a method of treating COPD by reducing the leukocyte count in a subject, said method comprising administering to the subject an effective amount of a RORγ inhibitor by an inhalation route.

In yet another embodiment, the present invention relates to a method of treating COPD by reducing the neutrophil count in a subject, said method comprising administering to the subject an effective amount of a RORγ inhibitor.

In yet another embodiment, the present invention relates to a method of treating COPD by reducing the neutrophil count in a subject, said method comprising administering to the subject an effective amount of a RORγ inhibitor by an inhalation route.

In yet another embodiment, the present invention relates to a method of treating COPD by reducing the macrophages count in a subject, said method comprising administering to the subject an effective amount of a RORγ inhibitor.

In yet another embodiment, the present invention relates to a method of treating COPD by reducing the macrophages count in a subject, said method comprising administering to the subject an effective amount of a RORγ inhibitor by an inhalation route.

In yet another embodiment, the present invention relates to a method of treating COPD by reducing the leukocyte or neutrophil or macrophages count or all three in a subject, said method comprising administering to the subject an effective amount of a RORγ inhibitor.

In yet another embodiment, the present invention relates to a method of treating COPD by reducing the leukocyte or neutrophil or macrophages count or all three in a subject, said method comprising administering to the subject an effective amount of a RORγ inhibitor by the inhalation route.

Preferably, the RORγ inhibitors used in the method of treatment in accordance with the present invention have an $IC_{50}$ for inhibiting human RORγ receptor activity of less than 1 micromolar or less than 700 nanomolar, or more preferably, less than 500 nanomolar.

Preferably, the RORγ inhibitors may be selected from Compound 1 and Compound 9 or a pharmaceutically acceptable salt thereof.

The $IC_{50}$ value is believed to be a measure of the effectiveness of a compound in inhibiting biological or biochemical function. This quantitative measure generally indicates molar concentration of a particular compound (or substance) that is needed to inhibit a given biological process by half. In other words, it is the half maximal (50%) inhibitory concentration (IC) of the compound. The $IC_{50}$ of a drug compound can be determined by constructing a concentration-response curve so as to examine the effect of different concentrations of inhibitor on reversing agonist activity. The $IC_{50}$ values can be calculated for a given inhibitor by determining the concentration needed to inhibit half of the maximum biological response of the agonist. These values can be used to compare the potency of two inhibitors As contemplated herein, the $IC_{50}$ value is measured by the following method. The inhibition of RORγ receptor activation is measured as inhibition of allylisothiocyanate (AITC) induced cellular uptake of radioactive calcium. A test solution of test compound is prepared in a suitable solvent using appropriate method. Human RORγ expressing CHO cells are grown in suitable medium. Cells are treated with test compounds followed by addition of AITC. Cells are washed and lysed. Radioactivity in the lysate is measured in Packard Top count after addition of liquid scintillant. The concentration response curves for compounds are plotted as a percentage of maximal response obtained in the absence of test inhibitor, and the $IC_{50}$ values are calculated from such concentration response curve by nonlinear regression analysis using GraphPad PRISM software.

In a preferred embodiment, the present invention relates to a method of treating asthma or COPD in a subject, said method comprising administering to the subject by the inhalation route an effective amount of a RORγ inhibitor having an $IC_{50}$ for inhibiting human RORγ receptor activity of less than 2 micromolar or less than 1 micromolar or preferably less than 700 nanomolar, or more preferably less than 500 nanomolar.

Asthma is clinically classified according to the frequency of symptoms, forced expiratory volume in 1 second (FEV1), peak expiratory flow rate and severity (e.g., acute, intermittent, mild persistent, moderate persistent, and severe persistent). Asthma may also be classified as allergic (extrinsic) or non-allergic (intrinsic), based on whether symptoms are precipitated by allergens or not. Asthma can also be categorized according to following types viz., nocturnal asthma, bronchial asthma, exercise induced asthma, occupational asthma, seasonal asthma, silent asthma, and cough variant asthma.

COPD, also known as chronic obstructive lung disease (COLD), chronic obstructive airway disease (COAD), or chronic obstructive respiratory disease (CORD), is believed to be the co-occurrence of chronic bronchitis (characterized by a long-term cough with mucus) and emphysema (characterized by destruction of the lungs over time), a pair of commonly co-existing diseases of the lungs in which the airways become narrowed. This leads to a limitation of the flow of air to and from the lungs, causing shortness of breath. An acute exacerbation of COPD is a sudden worsening of COPD symptoms (shortness of breath, quantity and color of phlegm) that typically lasts for several days and is believed to be triggered by an infection with bacteria or viruses or by environmental pollutants. Based on the FEV1 values, COPD can be classified as mild, moderate, severe and very severe.

Human airways are innervated by a generous supply of efferent, cholinergic, parasympathetic autonomic nerves. Motor nerves derived from the vagus form ganglia within and around the walls of the airways. Release of acetylcholine (ACh) at these sites results in stimulation of muscarinic receptors and subsequent airway smooth muscle contraction and release of secretions from the submucosal airway glands. Epithelial and inflammatory cells also generate ACh and express functional muscarinic receptors. Recent findings indicate that ACh, acting on muscarinic receptors, may contribute to the pathophysiology and pathogenesis of asthma and COPD.

In an embodiment, the present invention relates to a method of treating diseases mediated by IL-17 blockade in a subject in need thereof, said method comprising administering to the subject by an inhalation route an effective amount of Compound 1 or its pharmaceutically acceptable salt wherein the disorder is preferably COPD or lung emphysema.

Specifically, in an embodiment, the present invention relates to a method of treating COPD by reducing leukocyte or neutrophil or macrophages count or all three in a subject, said method comprising administering to the subject by an inhalation route a therapeutically effective amount of Compound 1 or its pharmaceutically acceptable salt. The therapeutically effective amount of Compound 1 or its pharmaceutically acceptable salt may range from about 0.1 mcg/kg to about 30 mg/kg.

In yet another specific embodiment, the present invention relates to a method of treating COPD by reducing leukocyte or neutrophil or macrophages count or all three in a subject, said method comprising administering to the subject by an inhalation route a therapeutically effective amount of Compound 9 or its pharmaceutically acceptable salt. The therapeutically effective amount of Compound 9 or its pharmaceutically acceptable salt may range from about 0.1 mcg/kg to about 30 mg/kg.

In another embodiment, the present invention relates to a method of treating COPD in a subject, said method comprising administering to the subject by an inhalation route a RORγ inhibitor in an amount ranging from about 0.1 mcg to about 30 mg. Preferably, the RORγ inhibitor is selected from Compound 1 or Compound 9 or a pharmaceutically acceptable salt thereof.

In one of the aspect of the present invention, the inhalation route comprises nasal or oral inhalation or both wherein the RORγ inhibitors are administered to intra-tracheal region of the subject. The compositions suitable for administration by the inhalation route may include dry powder inhaler (DPI) formulations, metered dose inhaler (MDI) formulations (including oral and nasal aerosols), nasal sprays, and formulations suitable for nebulization.

In an embodiment, the present invention relates to a method of treating COPD in a subject, said method comprising administering to the subject by the inhalation route an effective amount of a RORγ inhibitor having an $IC_{50}$ for inhibiting human RORγ receptor activity of less than 2 micromolar or preferably less than 1 micromolar, or preferably less than 700 nanomolar, or even more preferably less than 500 nanomolar.

The present invention also relates to a method of identifying a RORγ inhibitor useful for treating COPD by inhalation administration in a subject, said method comprising:
(a) determining an $IC_{50}$ for inhibiting human RORγ receptor activity of each of a plurality of compounds;
(b) selecting the compounds having an $IC_{50}$ for inhibiting human RORγ receptor activity of less than 2 micromolar;
(c) evaluating the in vivo activity of the identified compounds in a respiratory disorder model assay, wherein the compounds are administered by the inhalation route; and
(d) identifying the compounds to be effective for treating the respiratory disorder.

In another aspect, the present invention relates to a RORγ inhibitor having an $IC_{50}$ for inhibiting human RORγ receptor activity of less than less than 2 micromolar or less than 1 micromolar, or preferably less than 700 nanomolar, or even more preferably less than 500 nanomolar for treating COPD in a subject by administering an effective amount of the RORγ inhibitor by the inhalation route.

In yet another aspect, the present invention relates to a RORγ inhibitor having an $IC_{50}$ for inhibiting human RORγ receptor activity of less than less than 2 micromolar or less than 1 micromolar, or preferably less than 700 nanomolar, or even more preferably less than 500 nanomolar for treating COPD by reducing the leukocyte or neutrophil or macrophages count or all three in a subject by administering an effective amount of the RORγ inhibitor by the inhalation route, wherein such inhibition of human RORγ receptor activity is the principal therapeutic mode of action of the RORγ inhibitor. It is contemplated that inhibition of human RORγ receptor activity could be principal but not the exclusive mode of action of the RORγ inhibitor.

Particularly contemplated are RORγ inhibitors for which inhibition of human RORγ receptor activity is principal but not the exclusive mode of action of the RORγ inhibitor. For instance, the RORγ inhibitor can be compounds 1, 3, 6 and 9. Also particularly contemplated are RORγ inhibitors for which inhibition of human RORγ receptor activity is principal but not the exclusive mode of action of the RORγ inhibitor. For instance, the RORγ inhibitor can be compounds 2, 4, 5, 7, 8, 10 and 11.

Thus in a specific embodiment, the present invention relates to Compound 1 or its pharmaceutically acceptable salt for treating COPD in a subject by administering an effective amount of Compound 1 or its pharmaceutically acceptable salt by an inhalation route, wherein inhibition of human RORγ receptor activity is the principal therapeutic mode of action of Compound 1 or its pharmaceutically acceptable salt.

In yet another specific embodiment, the present invention relates to Compound 9 or its pharmaceutically acceptable salt for treating COPD in a subject by administering an effective amount of Compound 9 or its pharmaceutically acceptable salt by an inhalation route, wherein inhibition of human RORγ receptor activity is the principal therapeutic mode of action of Compound 9 or its pharmaceutically acceptable salt.

In an embodiment, the present invention relates to a RORγ inhibitor having an $IC_{50}$ for inhibiting human RORγ receptor activity of less than 2 micromolar or preferably less than 1 micromolar, or even more preferably less than 500 nanomolar for treating COPD in a subject by administering an effective amount of the RORγ inhibitor by an inhalation route.

Specifically, the RORγ inhibitor may be selected from Compound 1 and Compound 9 or a pharmaceutically acceptable salt thereof.

In another embodiment, the present invention provides use of an effective amount of a RORγ inhibitor having an $IC_{50}$ for inhibiting human RORγ receptor activity of less than 2 micromolar in the manufacture of a composition for inhalation administration for the treatment of COPD in a subject, wherein such inhibition of human RORγ receptor activity is the principal therapeutic mode of action of the RORγ inhibitor. It is contemplated that inhibition of human RORγ receptor activity is principal but not the exclusive mode of action of the RORγ inhibitor.

In an embodiment, the present invention relates to use of an effective amount of a RORγ inhibitor having an $IC_{50}$ for inhibiting human RORγ receptor activity of less than 2 micromolar or less than 1 micromolar, or preferably less than 700 nanomolar, or even more preferably less than 500 nanomolar in the manufacture of a composition for inhalation administration for the treatment of COPD in a subject.

Specifically, in an embodiment, the present invention relates to use of an effective amount of Compound 1 or its pharmaceutically acceptable salt in the manufacture of a composition for inhalation administration for the treatment of COPD in a subject.

Specifically, in yet another embodiment, the present invention relates to use of an effective amount of Compound 9 or its pharmaceutically acceptable salt in the manufacture of a composition for inhalation administration for the treatment of COPD in a subject.

In an embodiment, the present invention relates to use of an effective amount of a RORγ inhibitor having an $IC_{50}$ for inhibiting human RORγ receptor activity of less than 2 micromolar or less than 1 micromolar or preferably less than 700 nanomolar or more preferably less than 500 nanomolar in the manufacture of a composition for inhalation administration for the treatment of COPD by reducing the leukocyte or neutrophil or macrophages count or all three in a subject in need thereof.

Pharmaceutical Compositions

The present invention also provides pharmaceutical compositions for inhalation administration comprising a RORγ inhibitor having an $IC_{50}$ for inhibiting human RORγ receptor activity of less than 2 micromolar or preferably less than 1 micromolar, or even more preferably less than 500 nanomolar. Pharmaceutical compositions suitable for administration by the inhalation route include, but are not limited to dry powder inhaler (DPI) formulations, metered dose inhaler (MDI) formulations (including oral and nasal aerosols), nasal sprays, and formulations suitable for nebulization.

The inhalation may be administered by oral route or nasal route or both. The composition may be in the form of a metered dose inhaler, a dry powder inhaler, a nasal aerosol, a nasal spray or a nebulizer or any other suitable form of administration for oral or nasal inhalation. The device may be a single dose/unit dose type or reservoir type.

In a further aspect of the present invention, the pharmaceutical composition may comprise pharmaceutically acceptable excipients in addition to the RORγ inhibitor.

The pharmaceutical composition may include at least one pharmaceutically acceptable excipient, such as one or more of the following: diluents, glidants and lubricants, preservatives, buffering agents, chelating agents, polymers, surfactants, propellants and solvents. In the pharmaceutical composition as described herein, the frequency of dosing can be once daily (od) or two/three/four times a day.

It will be understood that various modifications may be made to the embodiments disclosed herein. Therefore the above description should not be construed as limiting, but merely as exemplifications of preferred embodiments.

The following examples are provided to enable one skilled in the art to practice the invention and are merely illustrative of the invention. The examples should not be read as limiting the scope of the invention.

EXAMPLES

Example 1: Determination of $IC_{50}$ of Exemplary RORγ Inhibitors of the Present Invention Protocol:

The compounds described herein were screened for RORγ inhibitor activity using the TR-FRET assay by Lantha Screen as described in *JBC* 2011, 286, 26: 22707-10; and *Drug Metabolism and Disposition* 2009, 37, 10: 2069-78

TR-FRET Assay for ROR Gamma:

The assay is based on the principle that binding of the agonist to the RORγ causes a conformational change around helix 12 in the ligand binding domain, resulting in higher affinity for the co-activator peptide. The Fluorescein-D22 co-activator peptide used in the assay is recruited in the absence of a ligand. Binding of the co-activator peptide, causes an increase in the TR-FRET signal while binding of an inhibitor decreases the recruitment of the co-activator peptide, causing a decrease in the TR-FRET signal compared to a control with no test compound. The assay was performed using a two-step procedure, pre-incubation step with the test compound followed by the detection step on addition of the anti-GST tagged terbium (Tb) and fluorescein tagged fluorophores as the acceptor.

Test compounds or reference compounds such as T0901317 (Calbiochem) were dissolved in dimethylsulfoxide (DMSO) to prepare 10.0 mM stock solutions and diluted to the desired concentration. The final concentration of DMSO in the reaction was 4% (v/v). The assay mixture was prepared by mixing 10 nM of the GST-tagged ROR gamma ligand binding domain (LBD) in the assay buffer containing 25 mM HEPES (pH 7.4), 100 mM NaCl, 5 mM DTT and 0.01% BSA with or without the desired concentration of the test compound. The reaction was incubated at 22° C. for 1 hour. The pre-incubation step was terminated by addition of the detection mixture containing 300 nM Fluorescein-D22 co-activator peptide and 10 nM lantha screen Tb-anti GST antibody into the reaction mixture. After shaking for 5 minutes the reaction was further incubated for 1 hour at room temperature and read at 4° C. on an Infinite F500 reader as per the kit instructions (Invitrogen). The inhibition by test compound was calculated based on the TR-FRET ratio of 520/495. The activity was calculated as a percent of the control reaction. $IC_{50}$ values were calculated from dose response curve by nonlinear regression analysis using GraphPad Prism software.

The compounds prepared were tested using the above assay procedure and the results obtained are given in Table 1. The compounds were found to have $IC_{50}$ values less than 50 nM.

TABLE 1

RORγ inhibitors having an $IC_{50}$ for inhibiting human RORγ receptor activity

| Compound No. | $IC_{50}$ value (nM) |
| --- | --- |
| Compound 1 | 4.26 |
| Compound 2 | 22.35 |
| Compound 3 | 5.517 |
| Compound 4 | 5.99 |

TABLE 1-continued

RORγ inhibitors having an IC$_{50}$ for inhibiting human RORγ receptor activity

| Compound No. | IC$_{50}$ value (nM) |
|---|---|
| Compound 5 | 17.36 |
| Compound 6 | 2.18 |
| Compound 7 | 0.615 |
| Compound 8 | 1.98 |
| Compound 9 | 18.44 |
| Compound 10 | 16.18 |
| Compound 11 | 25.71 |

Example 2: Efficacy Study of a RORγ Inhibitor on Cigarette Smoke (CS) Induced Pulmonary Inflammation Model in Male C57BL6/J Mice Male C57BL/6 mice were exposed alternately to cigarette smoke (10 Kentucky Research Cigarettes 3R4F) and fresh air for 50 minutes (10 seconds cigarette smoke+5 seconds air for 19 puffs per cigarette) twice daily for 7 days in a whole-body box exposure system (SIU24, ProMech Lab Holding AB, Sweden). Test compounds were sonicated in 1×PBS containing 0.005% tween 80. For localized delivery to lung, animals were administered vehicle or test compounds intranasally (i.n.) (40 μl per animal) under isoflurane anaesthesia, once or twice in a day, 1 hour before smoke exposure. Non-drug-treated air and smoked control animals were given vehicle before exposure to fresh air or smoke as appropriate. Animals were sacrificed 20 hours after the last smoke exposure and subjected to bronchoalveolar lavage (BAL). Total and differential BAL cell count was performed.

Animals were assigned to one of the following groups during experiment (Table 2)

TABLE 2

Efficacy study of RORγ inhibitor on cigarette smoke (CS) induced pulmonary inflammation model in male C57BL6/J mice

| Group | Group Code | Dose | CS Challenge | Number of animals/group |
|---|---|---|---|---|
| A | Air + Vehicle | 40 μl i.n.; od | − | 7 |
| B | CS + Vehicle | 40 μl i.n.; od | + | 7 |
| C | Compound 1 - 1 μg | 1 μg/ 40 μl i.n.; od | + | 7 |
| D | Compound 1 - 10 μg | 10 μg/ 40 μl i.n.; od | + | 7 |
| E | Compound 1 - 30 μg | 30 μg/ 40 μl i.n.; od | + | 7 |
| F | Compound 1 - 50 μg | 50 μg/ 40 μl i.n.; od | + | 7 |
| G | Compound 1 - 100 μg | 100 μg/ 40 μl i.n.; od | + | 7 |

Bronchoalveolar Lavage:

BAL was performed at approximately 20 hours after final smoke exposure. Animals were euthanized with an overdose of urethane, trachea was exposed and BAL was performed 4 times using 0.3 ml PBS. All aspirates of BAL were pooled and total numbers of cells were determined using a hemocytometer. BALf was centrifuged. The cell pellet collected after centrifugation was resuspended in 15 μL serum and used for preparation of smears.

For cell differentials, slides were stained with Leishman's stain and a differential cell count of 500 cells based on standard morphology was performed manually.

Calculations

The total number of Leukocytes type in each BAL sample was calculated using the formula:

$$\text{Total } No. \text{ of Leukocytes type} = \frac{\text{Total Leukocyte count} \times 10^5/\text{ml} \times \text{Percent Leukocytes type}}{100}$$

Percent inhibition of Leukocytes type was calculated using the following formula:

$$\% \text{ Inhibition of Leukocytes type} = \frac{Avg.\ Leukocytes_{(CS+Vehicle)} - Leukocytes_{(CS+Treatment)}}{Avg.\ Leukocytes_{(CS+Vehicle)} - Avg.\ Leukocytes_{(Air+Vehicle)}} \times 100$$

Data Analysis:

Total and differential cell count was determined in the BALf. The results were expressed as percent inhibition of leukocytes in BALf. The change in the treatments was statistically evaluated by ANOVA followed by Dunnett's multiple comparisons test.

Results

In the CS exposed animals treated with vehicle, significant increase in cell infiltration was observed compared to air exposed animals. Compound 1 significantly prevented CS mediated increase in total leukocyte count (TLC), neutrophils and macrophages in BALf (FIG. 1)

Conclusion

Compound 1 showed significant inhibition of pulmonary inflammation induced by cigarette smoke.

Example 3: Efficacy Study of a RORγ Inhibitor on Cigarette Smoke (CS) Induced Pulmonary Inflammation Model in Male C57BL6/J Mice The efficacy study for compound 3 as a RORγ inhibitor on cigarette smoke (CS) induced pulmonary inflammation model in male C57BL6/J mice was performed according to the procedure described in Example-2.

Animals were assigned to one of the following groups during experiment (Table 3).

TABLE 3

Efficacy study of RORγ inhibitor on cigarette smoke (CS) induced pulmonary inflammation model in male C57BL6/J mice

| Group | Group Code | Dose | CS Challenge | Number of animals/group |
|---|---|---|---|---|
| A | Air + 40 μl Vehicle | 40 μl i.n.; bid | − | 7 |
| B | CS + Vehicle 40 μl | 40 μl i.n.; bid | + | 7 |
| C | Compound 3 - 10 μg | 10 μg/ 40 μl i.n.; od | + | 7 |
| D | Compound 3 - 30 μg | 30 μg/ 40 μl i.n.; od | + | 7 |
| E | Compound 3 - 50 μg | 50 μg/ 40 μl i.n.; od | + | 7 |
| F | Compound 3 - 100 μg | 100 μg/ 40 μl i.n.; od | + | 7 |

Bronchoalveolar Lavage and data was analyzed according to the method described in Example 02.

Results

In the CS exposed animals treated with vehicle, significant increase in cell infiltration was observed compared to air exposed animals. Compound 3 significantly prevented CS mediated increase in total leukocyte count (TLC), neutrophils and macrophages in BALf (FIG. 2).

Conclusion

Compound 3 showed significant inhibition of pulmonary inflammation induced by cigarette smoke.

Example 4: Efficacy Study of a RORγ Inhibitor on Cigarette Smoke (CS) Induced Pulmonary Inflammation Model in Male C57BL6/J Mice The efficacy study for compound 6 as a RORγ inhibitor on cigarette smoke (CS) induced pulmonary inflammation model in male C57BL6/J mice was performed according to the procedure described in Example-2.

Animals were assigned to one of the following groups during experiment (Table 4)

TABLE 4

Efficacy study of RORγ inhibitor on cigarette smoke (CS) induced pulmonary inflammation model in male C57BL6/J mice

| Group | Group Code | Dose | CS Challenge | Number of animals/group |
|---|---|---|---|---|
| A | Air | 40 µl i.n.; bid | − | 7 |
| B | CS + 40 µl Vehicle, in, od | 40 µl i.n.; bid | + | 7 |
| C | Compound 6 - 1 µg | 1 µg/ 40 µl i.n.; od | + | 7 |
| D | Compound 6 - 3 µg | 3 µg/ 40 µl i.n.; od | + | 7 |
| E | Compound 6 - 10 µg | 10 µg/ 40 µl i.n.; od | + | 7 |
| F | Compound 6 - 30 µg | 30 µg/ 40 µl i.n.; od | + | 7 |
| G | Compound 6 - 50 µg | 50 µg/ 40 µl i.n.; od | + | 7 |
| H | Compound 6 - 100 µg | 100 µg/ 40 µl i.n.; od | + | 7 |

Bronchoalveolar Lavage and data was analyzed according to the method described in Example 02.

Results

In the CS exposed animals treated with vehicle, significant increase in cell infiltration was observed compared to air exposed animals. Compound 6 significantly prevented CS mediated increase in total leukocyte count (TLC), neutrophils and macrophages in BALf (FIG. 3).

Conclusion

Compound 6 showed significant inhibition of pulmonary inflammation induced by cigarette smoke.

Example 5: Efficacy Study of a RORγ Inhibitor on Cigarette Smoke (CS) Induced Pulmonary Inflammation Model in Male C57BL6/J Mice The efficacy study for compound 9 as a RORγ inhibitor on cigarette smoke (CS) induced pulmonary inflammation model in male C57BL6/J mice was performed according to the procedure described in Example-2.

Animals were assigned to one of the following groups during experiment (Table 5)

TABLE 5

Efficacy study of RORγ inhibitor on cigarette smoke (CS) induced pulmonary inflammation model in male C57BL6/J mice

| Group | Group Code | Dose | CS Challenge | Number of animals/group |
|---|---|---|---|---|
| A | Air | 40 µl i.n.; bid | − | 7 |
| B | CS + 40 µl Vehicle, in, od | 40 µl i.n.; bid | + | 7 |
| C | Compound 9 - 0.3 µg | 0.3 µg/ 40 µl i.n.; od | + | 7 |
| D | Compound 9 - 1 µg | 1 µg/ 40 µl i.n.; od | + | 7 |
| E | Compound 9 - 10 µg | 10 µg/ 40 µl i.n.; od | + | 7 |
| F | Compound 9 - 30 µg | 30 µg/ 40 µl i.n.; od | + | 7 |
| G | Compound 9 - 50 µg | 50 µg/ 40 µl i.n.; od | + | 7 |

Bronchoalveolar Lavage and data was analyzed according to the method described in Example 02.

Results

In the CS exposed animals treated with vehicle, significant increase in cell infiltration was observed compared to air exposed animals. Compound 9 significantly prevented CS mediated increase in total leukocyte count (TLC), neutrophils and macrophages in BALf (FIG. 4).

Conclusion

Compound 9 showed significant inhibition of pulmonary inflammation induced by cigarette smoke.

Example 6: Efficacy Study of a RORγ Inhibitor on Inflammation and Emphysema in the Animals Chronically Exposed to Cigarette Smoke (CS)

Male C57BL/6 mice were exposed alternately to CS (10 Kentucky Research cigarettes 3R4F) and fresh air for 50 minutes once daily for 5 days in a week for 13 weeks in a whole-body box exposure system (SIU24, ProMech Lab Holding AB, Sweden). Compound 1 was sonicated in 1×PBS containing 0.005% tween 80. For localized delivery to lung, animals were dosed with different doses of compound 1 intranasally (i.n.) (40 µl per animal) under isoflurane anaesthesia, once daily, 1 hour before smoke exposure. Non-drug-treated air and smoked control animals were given vehicle before exposure to fresh air or smoke as appropriate. Animals were sacrificed 20 hours after the last smoke exposure and subjected to BAL. Total and differential BAL cell count was performed.

After BAL, lungs were fixed intra-tracheally with neutral buffered formalin (10%) at a pressure of 20 cm $H_2O$ for 45 minutes. The trachea was tied off, and the lungs along with heart were removed and stored in neutral buffered formalin (10%). The left lung of mice was cut in longitudinal vertical direction and embedded in paraffin, and was sectioned at a thickness of 5 µm and stained with hematoxylin and eosin. For each animal, 3 random fields of the lung sections were captured at 100× magnification using microscope camera. Major airways and vasculature was generally avoided in selecting fields to focus on peripheral parenchyma. Mean linear intercept (Lm) was measured by means of superimposing 500×500-µm grid with 100-µm squares. Lm was calculated as the total length of the grid lines divided by the number of alveolar intercepts Animals were assigned to one of the following groups during experiment (Table 6).

TABLE 6

Efficacy study of a RORγ inhibitor on inflammation and emphysema in the animals chronically exposed to cigarette smoke (CS)

| Group | Group Code | Dose | CS Challenge | Number of animals/group |
|---|---|---|---|---|
| A | Air + Vehicle | 40 µl i.n.; od | − | 7 |
| B | CS + Vehicle | 40 µl i.n.; od | + | 7 |
| C | Compound 1 - 10 µg | 10 µg/ 40 µl i.n.; od | + | 7 |
| D | Compound 1 - 50 µg | 50 µg/ 40 µl i.n.; od | + | 7 |
| E | Compound 1 - 100 µg | 100 µg/ 40 µl i.n.; od | + | 7 |

Bronchoalveolar Lavage and data was analyzed according to the method described in Example 02.

Results

In the CS exposed animals treated with vehicle, significant increase in cell infiltration was observed compared to air exposed animals. Compound 1 significantly prevented CS mediated increase in total leukocyte count (TLC), neutrophils and macrophages in BALf (FIG. 5). Significant increase in mean linear intercept (µm), an index of emphysema, was observed in cigarette smoke compared to air exposed animals. Compound 1 significantly prevented cigarette smoke induced emphysema (FIG. 6).

Conclusion

Compound 1 showed significant inhibition of pulmonary inflammation as well emphysema in the animals chronically exposed to CS.

Example 7: Efficacy Study of a RORγ Inhibitor on Poly (I:C) Induced COPD Exacerbation in Female C57BL/6 Mice Female C57BL/6 mice were exposed alternately to cigarette smoke (10 Kentucky Research Cigarettes 3R4F) and fresh air for 50 minutes (10 seconds cigarette smoke+5 seconds air for 19 puffs per cigarette) twice daily for 15 days in a whole-body box exposure system (SIU24, ProMech Lab Holding AB, Sweden). Test compounds were sonicated in 1×PBS containing 0.005% tween 80. For localized delivery to lung, animals were administered vehicle or test compounds intranasally (i.n.) 50 µl per animal under isoflurane anesthesia. On day 15, one hour after the cigarette smoke exposure, animals were administered with Compound 1 and Roflumilast according to their respective treatment group as mentioned in Table No. 6. Non-drug treated animals were administered with vehicle. Poly (I:C) was administered 1 hour after drug treatment to all the groups except Room Air (RA) and Cigarette Smoke (CS) groups. Forty eight hour after Poly (I:C) administration, animals were sacrificed and subjected to BAL. Total and differential BAL cell count was performed.

Animals were assigned to one of the following groups during experiment (Table 7).

TABLE 7

Efficacy study of a RORγ inhibitor on Poly (I:C) induced COPD exacerbation in female C57BL/6 mice

| Group No. | Group Code | Dose | CS Challenge | Poly IC Challenge | Number of animals/group |
|---|---|---|---|---|---|
| A | RA exposed | Vehicle 50 µL, i.n., q.d. | − | − | 10 |
| B | CS exposed | Vehicle 50 µL, i.n., q.d. | + | − | 10 |
| C | RA & Poly (I:C) | Vehicle 50 µL, i.n., q.d. | − | + | 10 |
| D | CS & Poly (I:C) | Vehicle 50 µL, i.n., q.d. | + | + | 10 |
| E | CS & Poly (I:C) + Roflumilast | Roflumilast - 50 µg, i.n., b.i.d. on day 15 & 16 | + | + | 10 |
| F | CS & Poly (I:C) + Compound 1 | Compound 1 - 50 µg, i.n., q.d. on day 15 | + | + | 10 |
| G | CS & Poly (I:C) + Compound 1 | Compound 1 - 100 µg, i.n., q.d. on day 15 | + | + | 10 |

Bronchoalveolar Lavage:

BAL was performed at approximately 48 hour after Poly (I:C) administration. Animals were euthanized with an overdose of urethane, trachea was exposed and BAL was performed 4 times using 0.3 ml PBS. All aspirates of BAL were pooled and total numbers of cells were determined using a hemocytometer. BALf was centrifuged. The cell pellet collected after centrifugation was re-suspended in 15 µL serum and used for preparation of smears.

For cell differentials, slides were stained with Leishman's stain and a differential cell count of 500 cells based on standard morphology was performed manually.

Calculations

The percentage of inhibition was calculated by using the following formula:

The total number of Leukocytes type in each BAL sample was calculated using the formula:

$$\text{Total } No. \text{ of Leukocytes} = \frac{\text{Total Leukocyte count } \times 10^5/\text{ml} \times \text{Percent Leukocytes type}}{100}$$

Percent inhibition of Leukocyte type was calculated using the following formula:

$$\% \text{ Inhibition of Leukocytes type} = \frac{Avg.\ Leukocytes_{(CS\ \&poly\ I:C)} - Leukocytes_{(CS\ \&poly\ I:C+Treatment)}}{Avg.\ Leukocytes_{(CS\ \&poly\ I:C)} - Avg.\ Leukocytes_{(CS)}} \times 100$$

Data Analysis

Total and differential cell count was determined in the BALf. The results were expressed as percent inhibition of leukocytes in BALf. The change in the treatments was statistically evaluated by One-way ANOVA followed by Bonferroni's Multiple Comparison Test.

Results

In the mice exposed to CS and poly (I:C) there was significant increase in cellular infiltration compared to those exposed to CS alone. Compound 1 significantly prevented CS and poly (I:C) mediated increase in total leukocyte count (TLC), neutrophils and lymphocytes in BALf (FIG. 7).

Conclusion

Compound 1 showed significant inhibition of exacerbations induced by Poly (I:C) and cigarette smoke in mice.

Example 8: Ex-Vivo Evaluation of ROR γt Inhibitors for IL-17 Inhibition from BAL Cells and PBMCs of COPD Patients Ex vivo effect of ROR γt inhibitors were evaluated on tissue samples of eligible subjects suffering from moderate (Stage II), severe (Stage III) to very severe (Stage IV) COPD classified in accordance with GOLD guidelines.

Bronchoalveolar Lavage Cells Isolation

Flexible fiber optic bronchoscopy was performed on 6 eligible subjects (COPD patients) after written valid consent and lignocaine nebulization. Bronchoscope was wedged into bronchus, pre-warmed sterile saline solution instilled into the lobes and bronchoalveolar lavage was collected in sterile container on ice. The filtrate was passed through the cell strainer for removing the particulate matter and centrifuged at 2000 rpm for 10 mins. The BAL cell pellet obtained was further treated with ACK buffer to lyse out the RBCs. Isolated BAL cells per suspended in 10% FBS containing medium.

PBMC Isolation

Blood was collected in a heparin tube prior to bronchoscopy. 1:1 diluted blood was layered over Histopaque and centrifuged at 400 g, 30 min, at room temperature. The PBMC layer at the interface was aspirated and washed twice with PBS prior to re-suspension in 10% FBS containing media.

Cell Culture

PBMCs or BAL cells were seeded at $1-2\times10^5$ cells per well onto 96-well flat bottomed plates pre-coated with 2 μg/ml of CD2 antibody (LEAF Purified, Biolegend, #300212) and 10 μg/ml of CD3 antibody (Purified NA/LE, BD, #555329). This was followed by the pre-treatment with compounds (concentrations ranging from 1 nM to 10 uM) and roflumilast for one hour prior to addition of 2 μg/ml of soluble CD28 antibody (LEAF purified, Biolegend, #302914). BAL cells and PBMC were then incubated at 37° C. for 72 hrs in 5% CO2 incubator, after which supernatants were collected and stored at −80° C. prior to cytokine analysis.

Cytokine Analysis

Supernatants were analysed for IL-17A using either the High Sensitivity ELISA (eBioscience), or the LEGEND MAX™ ELISA kit (Biolegend) according to the manufacturer's instructions.

Calculations

IL-17 cytokine concentrations in the supernatants were determined from the standard curve plot. Percent inhibition for each set treated with compound was calculated using the formula:

Percent inhibition={100−(pg/ml of test compound/pg/ml of control×100)}.

$IC_{50}$ values were calculated from the dose response curves by nonlinear regression analysis using GraphPad Prism Software.

Results

ROR γt inhibitors showed a concentration dependent inhibition of anti CD2/3/28 stimulated IL-17 release from COPD lung BAL cells and PBMC. The average $IC_{50}$ values for these compounds in BAL and PBMC are represented in the Tables 8 and 9 respectively. Hence in conclusion, the test compounds showed pharmacological effect of pro-inflammatory IL-17 inhibition from stimulated lung BAL cells as well as peripheral PBMCs from COPD patients.

TABLE 8

RORγ inhibitors having an $IC_{50}$ for IL-17 inhibition from BAL cells

| Compound No. | No. of patients | BAL IL-17 $IC_{50}$ (nM) |
| --- | --- | --- |
| Compound 1 | 3 | 350.4 |
| Compound 9 | 3 | 2392 |
| Compound 10 | 2 | 720 |
| Compound 11 | 1 | 2698 |
| Roflumilast | 3 | 6.75% at 10 μM |

TABLE 9

RORγ inhibitors having an $IC_{50}$ for IL-17 inhibition from PBMC cells

| Compound No. | No. of patients | PBMC IL-17 $IC_{50}$ (nM) |
| --- | --- | --- |
| Compound 1 | 3 | 147 |
| Compound 9 | 3 | 360.2 |
| Compound 10 | 2 | 367 |
| Compound 11 | 1 | 84.05 |
| Roflumilast | 3 | 20.17% at 10 μM |

Although the invention herein has been described with reference to particular embodiments, it is to be understood that these embodiments are merely illustrative of the principles and application of the present invention. It is therefore to be understood that numerous modifications may be made to the illustrative embodiments and that other arrangements may be devised without departing from the spirit and scope of the present invention as described.

All publications, patents, and patent applications cited in this application are herein incorporated by reference to the same extent as if each individual publication, patent, or patent application was specifically and individually indicated to be incorporated herein by reference.

We claim:

1. A method of treating chronic obstructive pulmonary disease (COPD) in a subject, the method comprising administering to the subject an effective amount of a RORγ inhibitor by inhalation route, wherein the RORγ inhibitor is selected from compounds of formula (I)

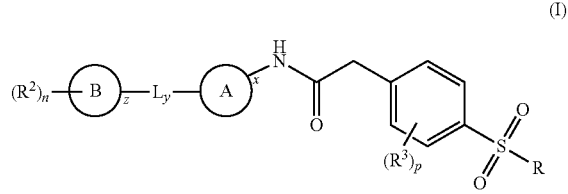

(I)

or a pharmaceutically acceptable salt thereof, wherein,

Ring A is

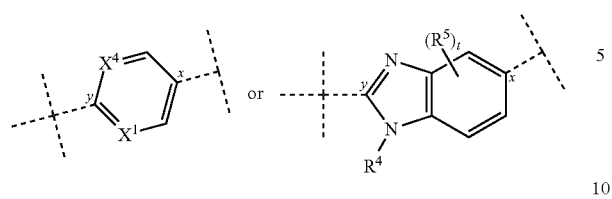

X¹ and X⁴, which may be same or different, are each independently selected from N, CH and CR¹;

Ring B is selected from phenyl, pyridinyl, benzimidazolyl, indolyl, [1,2,4]triazolo[4,3-a]pyridinyl and [1,2,4]oxadiazolyl;

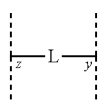

is selected from

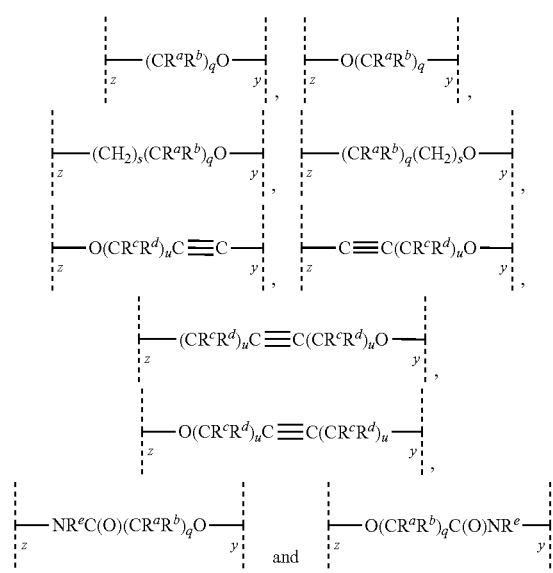

x, y and z represents point of attachment;

R is selected from $C_{1-8}$alkyl and halo$C_{1-8}$alkyl;

each occurrence of $R^1$ is independently selected from halogen, cyano, hydroxyl and $C_{1-8}$alkyl;

each occurrence of $R^2$ is independently selected from halogen, cyano, hydroxyl, $C_{1-8}$alkyl, $C_{1-8}$alkoxy, halo$C_{1-8}$alkyl, halo$C_{1-8}$alkoxy, hydroxy$C_{1-8}$alkyl, $C_{3-6}$cycloalkyl, $C_{3-6}$cycloalkyl$C_{1-8}$alkyl and 4-chloro-phenyl;

each occurrence of $R^3$ is independently selected from halogen, cyano, hydroxyl and $C_{1-4}$alkyl;

$R^4$ is selected from hydrogen, —$(CH_2)_2N(CH_3)_2$, $C_{1-8}$alkyl, halo$C_{1-8}$alkyl, $C_{3-6}$cycloalkyl and $C_{3-6}$cycloalkyl$C_{1-8}$alkyl;

each occurrence of $R^5$ is independently selected from halogen, cyano, hydroxyl and $C_{1-8}$alkyl;

each occurrence of $R^a$ and $R^b$, which may be same or different, are each independently selected from halogen, $C_{1-8}$alkyl, halo$C_{1-8}$alkyl and $C_{1-8}$alkoxy; or $R^a$ and $R^b$ together with the carbon atom to which they are attached, form a cyclopropyl, cyclobutyl, cyclopentyl, cyclohexyl, tetrahydro-2H-pyran-4-yl, oxetan-3-yl, N-methyl-piperidin-4-yl or piperidin-4-yl ring;

each occurrence of $R^c$ and $R^d$, which may be same or different, are each independently selected from hydrogen, $C_{1-8}$alkyl, halo$C_{1-8}$alkyl and $C_{1-8}$alkoxy; or $R^c$ and $R^d$ together with the carbon atom to which they are attached, form a $C_{3-6}$cycloalkyl ring;

$R^e$ is selected from $C_{1-8}$alkyl, halo$C_{1-8}$alkyl and $C_{3-6}$cycloalkyl;

'n' is 0, 1, 2 or 3;

'p' is 0, 1 or 2;

'q' is 1 or 2;

's' is 1, 2 or 3;

't' is 0, 1 or 2; and

'u' is 1 or 2.

2. The method according to claim 1, wherein the RORγ inhibitor is Compound 1, structurally represented as

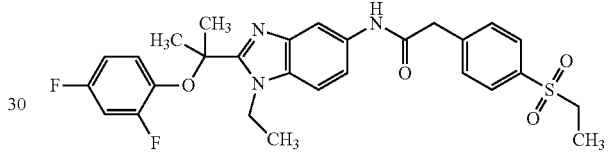

or a pharmaceutically acceptable salt thereof.

3. A method of treating COPD in a subject, said method comprising administering to the subject an effective amount of a RORγ inhibitor by inhalation route, wherein the RORγ inhibitor is Compound 1, structurally represented as

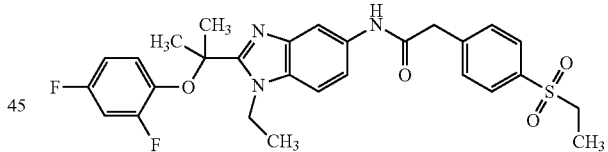

or a pharmaceutically acceptable salt thereof.

4. The method according to claim 1, wherein the RORγ inhibitor is Compound 9, structurally represented as

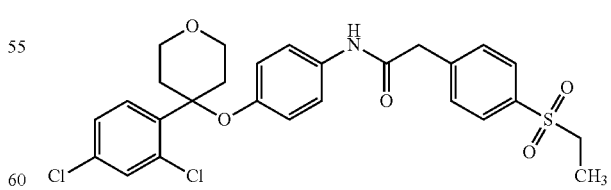

or a pharmaceutically acceptable salt thereof.

5. A method of treating COPD in a subject, said method comprising administering to the subject an effective amount of a RORγ inhibitor by inhalation route, wherein the RORγ inhibitor is Compound 9, structurally represented as

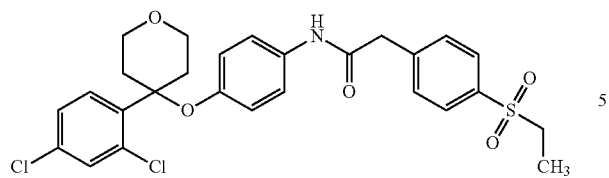
or a pharmaceutically acceptable salt thereof.
* * * * *